US008840882B2

(12) United States Patent  
Kink et al.

(10) Patent No.: US 8,840,882 B2  
(45) Date of Patent: Sep. 23, 2014

(54) MODIFIED RIBONUCLEASES

(75) Inventors: John A. Kink, Madison, WI (US); Laura E. Strong, Stoughton, WI (US); Vladimir Trubetskoy, Middleton, WI (US); Mark N. Shahan, Madison, WI (US)

(73) Assignee: Quintessence Biosciences, Inc., Madison, WI (US)

( * ) Notice: Subject to any disclaimer, the term of this patent is extended or adjusted under 35 U.S.C. 154(b) by 364 days.

(21) Appl. No.: 11/823,334

(22) Filed: Jun. 25, 2007

(65) Prior Publication Data

US 2008/0025964 A1   Jan. 31, 2008

Related U.S. Application Data

(60) Provisional application No. 60/816,179, filed on Jun. 23, 2006.

(51) Int. Cl.
- *A61K 38/46* (2006.01)
- *C12N 9/22* (2006.01)

(52) U.S. Cl.
USPC .......................................... 424/94.6; 435/199

(58) Field of Classification Search
CPC ..... A61K 2300/00; A61K 38/00; C12N 9/22; C12N 9/16; C12N 9/18
See application file for complete search history.

(56) References Cited

U.S. PATENT DOCUMENTS

| | | |
|---|---|---|
| 4,424,311 A | 1/1984 | Nagaoka |
| 4,708,930 A | 11/1987 | Kortright |
| 4,743,543 A | 5/1988 | Kortright |
| 4,892,935 A | 1/1990 | Yoshida |
| 4,914,021 A | 4/1990 | Toth |
| 4,918,164 A | 4/1990 | Hellstrom |
| 4,921,789 A | 5/1990 | Salem |
| 4,921,790 A | 5/1990 | O'brien |
| 4,939,240 A | 7/1990 | Chu |
| 4,963,484 A | 10/1990 | Kufe |
| 5,053,489 A | 10/1991 | Kufe |
| 5,096,815 A | 3/1992 | Ladner et al. |
| 5,110,911 A | 5/1992 | Samuel |
| 5,198,346 A | 3/1993 | Ladner et al. |
| 5,200,182 A | 4/1993 | Kiczka |
| 5,223,409 A | 6/1993 | Ladner et al. |
| 5,270,163 A | 12/1993 | Gold |
| 5,270,204 A | 12/1993 | Vallee et al. |
| 5,286,487 A | 2/1994 | Vallee et al. |
| 5,286,637 A | 2/1994 | Veronese et al. |
| 5,359,030 A | 10/1994 | Ekwuribe |
| 5,389,537 A | 2/1995 | Raines |
| 5,446,090 A | 8/1995 | Harris |
| 5,475,096 A | 12/1995 | Gold |
| 5,512,443 A | 4/1996 | Schlom |
| 5,545,530 A | 8/1996 | Satomura |
| 5,559,212 A | 9/1996 | Ardelt |
| 5,562,907 A | 10/1996 | Arnon |
| 5,660,827 A | 8/1997 | Thorpe et al. |
| 5,672,662 A | 9/1997 | Harris |
| 5,693,763 A | 12/1997 | Codington |
| 5,733,731 A | 3/1998 | Schatz et al. |
| 5,739,208 A | 4/1998 | Harris |
| 5,786,457 A | 7/1998 | Nett et al. |
| 5,808,005 A | 9/1998 | Codington |
| 5,811,238 A | 9/1998 | Stemmer et al. |
| 5,824,544 A | 10/1998 | Armentano et al. |
| 5,824,784 A | 10/1998 | Kinstler |
| 5,830,721 A | 11/1998 | Stemmer et al. |
| 5,830,730 A | 11/1998 | German et al. |
| 5,837,458 A | 11/1998 | Minshull et al. |
| 5,840,296 A | 11/1998 | Raines et al. |
| 5,840,840 A | 11/1998 | Rybak et al. |
| 5,855,866 A | 1/1999 | Thorpe |
| 5,866,119 A | 2/1999 | Bandman et al. |
| 5,872,154 A | 2/1999 | Wilson et al. |
| 5,885,808 A | 3/1999 | Spooner et al. |
| 5,892,019 A | 4/1999 | Schlom |
| 5,892,020 A | 4/1999 | Mezes |
| 5,900,461 A | 5/1999 | Harris |
| 5,932,462 A | 8/1999 | Harris |
| 5,955,073 A | 9/1999 | Rybak et al. |

(Continued)

FOREIGN PATENT DOCUMENTS

| | | |
|---|---|---|
| EP | 1316318 | 6/2003 |
| JP | 2003-206236 | 7/2003 |

(Continued)

OTHER PUBLICATIONS

Josef Matousek et al. "PEG chains increase aspermatogenic and antitumor activity of RNase A and BS-RNase enzymes" Journal of Controlled Release 82 (2002) 29-37.*
Suzuki et al. "Engineering receptor-mediated cytotoxicity into human ribonucleases by steric blockade of inhibitor interaction" Nature Biotechnology vol. 17 Mar. 1999 pp. 265-270.*
Veronese I "Surface Modification of Proteins" Applied Biochemistry and Biotechnology, vol. 11 , 1985, pp. 141-152.*
Veronese II "Peptide and protein PEGylation:a review of problems and solutions" Biomaterials 22 (2001) 405}417.*
Leland et al. "Endowing Human Pancreatic Ribonuclease with Toxicity for Cancer Cells" The Journal of Biological Chemistry, vol. 276, No. 46, Issue of Nov. 16, pp. 43095-43102, 2001.*
Leland, P.A. et al., "Cancer Chemotherapy—Ribonucleases to the Rescue," Chem and Biology. Apr. 2001, 8:405-413.

(Continued)

*Primary Examiner* — Jennifer McDonald
*Assistant Examiner* — Qing Xu
(74) *Attorney, Agent, or Firm* — David A. Casimir; Casimir Jones, S.C.

(57) ABSTRACT

The present invention relates generally to conjugates of human ribonucleases and water-soluble polymers, compositions comprising the conjugates and methods of using the same. In particular, the present invention provides conjugates of human ribonucleases and one or more water-soluble polymer compositions (e.g., to increase serum half-life and a pharmacokinetic profile, in vivo biological activity, stability, and/or reduce host immune response to the protein in vivo) as well as methods of using the conjugates in the therapy, treatment, and/or prevention of disease (e.g., cancer).

5 Claims, 20 Drawing Sheets

(56) References Cited

U.S. PATENT DOCUMENTS

| | | | |
|---|---|---|---|
| 5,981,225 | A | 11/1999 | Kochanek et al. |
| 5,990,237 | A | 11/1999 | Bentley |
| 5,994,106 | A | 11/1999 | Kovesdi et al. |
| 5,994,128 | A | 11/1999 | Fallaux et al. |
| 5,994,132 | A | 11/1999 | Chamberlain et al. |
| 6,001,557 | A | 12/1999 | Wilson et al. |
| 6,019,978 | A | 2/2000 | Ertl et al. |
| 6,033,908 | A | 3/2000 | Bout et al. |
| 6,045,793 | A | 4/2000 | Rybak et al. |
| 6,051,230 | A | 4/2000 | Thorpe et al. |
| 6,077,499 | A | 6/2000 | Griffiths et al. |
| 6,083,477 | A | 7/2000 | Goldenberg |
| 6,183,744 | B1 | 2/2001 | Goldenberg |
| 6,197,528 | B1 | 3/2001 | Wu et al. |
| 6,214,966 | B1 | 4/2001 | Harris |
| 6,271,369 | B1 | 8/2001 | Torrence et al. |
| 6,280,991 | B1 | 8/2001 | Raines |
| 6,312,694 | B1 | 11/2001 | Thorpe et al. |
| 6,348,558 | B1 | 2/2002 | Harris |
| 6,362,254 | B2 | 3/2002 | Harris |
| 6,362,276 | B1 | 3/2002 | Harris |
| 6,395,276 | B1 | 5/2002 | Rybak et al. |
| 6,399,068 | B1 | 6/2002 | Goldenberg |
| 6,406,897 | B1 | 6/2002 | Kim et al. |
| 6,416,758 | B1 | 7/2002 | Thorpe et al. |
| 6,428,785 | B1 | 8/2002 | Gokcen |
| 6,432,397 | B1 | 8/2002 | Harris |
| 6,437,025 | B1 | 8/2002 | Harris |
| 6,448,369 | B1 | 9/2002 | Bentley |
| 6,515,100 | B2 | 2/2003 | Harris |
| 6,541,543 | B2 | 4/2003 | Harris |
| 6,541,619 | B1 | 4/2003 | Park et al. |
| 6,610,281 | B2 | 8/2003 | Harris |
| 6,649,383 | B1 | 11/2003 | Cheung |
| 6,649,393 | B1 | 11/2003 | Youle et al. |
| 6,653,104 | B2 | 11/2003 | Goldenberg |
| 6,664,331 | B2 | 12/2003 | Harris |
| 6,676,941 | B2 | 1/2004 | Thorpe et al. |
| 6,737,505 | B2 | 5/2004 | Bentley |
| 6,828,401 | B2 | 12/2004 | Nho |
| 6,838,076 | B2 | 1/2005 | Patton |
| 6,864,327 | B2 | 3/2005 | Bentley |
| 6,864,350 | B2 | 3/2005 | Harris |
| 6,894,025 | B2 | 5/2005 | Harris |
| 6,962,702 | B2 | 11/2005 | Hansen et al. |
| 7,033,572 | B2 | 4/2006 | Goldenberg |
| 7,125,541 | B2 | 10/2006 | Thorpe et al. |
| 7,199,223 | B2 | 4/2007 | Bossard |
| 7,355,019 | B2 | 4/2008 | Backer et al. |
| 7,416,875 | B2 | 8/2008 | Raines et al. |
| 7,476,725 | B2 | 1/2009 | Zaplisky |
| 8,003,111 | B2 | 8/2011 | Chang et al. |
| 8,029,782 | B2 | 10/2011 | Klink et al. |
| 8,216,567 | B2 | 7/2012 | Klink et al. |
| 2001/0049434 | A1* | 12/2001 | Conklin ............... 536/23.1 |
| 2002/0006379 | A1 | 1/2002 | Hansen et al. |
| 2002/0037289 | A1 | 3/2002 | Thorpe et al. |
| 2002/0048550 | A1 | 4/2002 | Vallera et al. |
| 2002/0106359 | A1 | 8/2002 | Gokcen |
| 2002/0119153 | A1 | 8/2002 | Thorpe et al. |
| 2002/0187153 | A1 | 12/2002 | Goldenberg |
| 2003/0031669 | A1 | 2/2003 | Goldenberg |
| 2003/0114368 | A1 | 6/2003 | Rybak |
| 2003/0219785 | A1 | 11/2003 | Hallahan et al. |
| 2005/0158273 | A1 | 7/2005 | Harris |
| 2005/0181449 | A1 | 8/2005 | Kozlowski |
| 2005/0221431 | A1 | 10/2005 | Backer et al. |
| 2005/0261232 | A1* | 11/2005 | Strong et al. ............ 514/44 |
| 2005/0287113 | A1 | 12/2005 | Zaplisky |
| 2006/0292137 | A1 | 12/2006 | Raines et al. |
| 2007/0166278 | A1 | 7/2007 | Veronese |
| 2008/0025964 | A1 | 1/2008 | Kink |
| 2008/0095755 | A1 | 4/2008 | Kink |

FOREIGN PATENT DOCUMENTS

| | | |
|---|---|---|
| WO | 91/01758 | 2/1991 |
| WO | 96/21469 | 7/1996 |
| WO | WO 97/38134 | 10/1997 |
| WO | WO 98/33941 | 8/1998 |
| WO | 99/02685 | 1/1999 |
| WO | WO 99/02685 | 1/1999 |
| WO | WO 99/07724 | 2/1999 |
| WO | 00/09675 | 2/2000 |
| WO | WO 00/09675 | 2/2000 |
| WO | 00/12738 | 3/2000 |
| WO | WO 00/12738 | 3/2000 |
| WO | 0031242 | 6/2000 |
| WO | 01/94547 | 12/2001 |
| WO | WO 02/02630 | 1/2002 |
| WO | WO 03/031581 | 4/2003 |
| WO | 2007149594 | 12/2007 |

OTHER PUBLICATIONS

Psarras, K, et al., "Human pancreatic RNase1-human epidermal growth factor fusion: An entirely human immunotoxin analog with cytotoxic properties against squamous cell carcinomas," Protein Eng, 1998, 11:1285-1292.

Ike Y., et al., "Solid phase synthesis of polynucleotides,"Nucleic Acids Research, (1983) 11(2), pp. 477-488.

Eckert K., et al., "DNA Polymerase Fidelity and the Polymerase Chain Reaction," PCR Methods and Applications, (1991) 1(1), pp. 17-24.

Futami J., et al., "Inhibition of cell growth by a fused protein of human ribonuclease 1 . . . " Protein Engineering, (1999) 12(11) pp. 1013-1018.

Pous J., et al, "A Fully Human Antitumor ImmunoRNase Selective for ErbB-2-Positive Carcinomas," Acta Crystallogr D Biol Crystallogr., (2001) 57, pp. 498-505.

Terzyan S.S., et al, "The Three-dimensional Structure of Human RNase 4, Unliganded and Complexed with d(Up), Reveals the Basis for its Uridine Selectivity," J Mol. Biol., (1999) 285, pp. 205-214.

Kozlowski A, et al., "Development of pegylated interferons for the treatment of chronic hepatitis C." 2001 BioDrugs, 15:419-429.

Domachowske et al., "Evolution of antiviral activity in the ribonuclease A gene superfamily . . . ," Nucleic Acids Res 26 (23): 5327-32 (1998).

Sorrentino and Glitz, "Ribonuclease activity and substrate preference of human eosinophil cationic protein (ECP)" 1991 FEBS Lett. 288:23-6.

Hamachi et al., "Design and semisynthesis of spermine-sensitive ribonucleases S'" 1999 Bioorg Med Chem Lett 9:1215-1218.

Goldberg and Baldwin, "A specific transition state for S-peptide combining with folded S-protein and then refolding," 1999 PNAS 96:2019-2024.

Asai, T. et al., "An interaction between S tag and S protein derived from human ribonuclease 1 allows site-specific conjugation of an enzyme to an antibody for targeted drug delivery," 2005 J Immun Meth, 299:63-76.

Backer M et al., "Adapter Protein for Site-Specific conjugation of Payloads for Targeted Drug Delivery," 2004 Bioconjugate Chem 15:1021-1029.

Backer, M.V. et al., 2003, "Humanized docking system for assembly of targeting drug delivery complexes," J Cont Release, 89:499-511.

Kinstler et al., "Mono-N-terminal poly(ethylene glycol)-protein conjugates," 2002 Advanced Drug Delivery Reviews 54:477-485.

Roberts et al. "Chemistry for peptide and protein PEGylation," 2002 Advanced Drug Delivery Reviews 54:459-476.

Miller, K.D. and Sledge, G.W. Jr, "Taxanes in the treatment of breast cancer: a prodigy comes of age," 1999 Cancer Investigation, 17:121-136.

Haldar et al., "Bcl2 Is the Guardian of Microtubule Integrity," 1997 Cancer Research 57:229-233.

Lanni et al., "p53-independent apoptosis induced by paclitaxel through an indirect mechanism," 1997 Proc Natl Acad Sci 94:9679-9683.

(56) References Cited

OTHER PUBLICATIONS

Tortora et al., "Synergistic Inhibition of Growth and Induction of Apoptosis by 8-Chloro-cAMP and Paclitaxel or Cisplatin in Human Cancer Cells," 1997 Cancer Res 57:5107-5111.
Zaffaroni et al., "Induction of apoptosis by taxol and cisplatin and effect on cell cycle-related proteins in cisplatin-sensitive and -resistant human ovarian cancer cells," 1998 Brit. J. Cancer 77:1378-1385.
Ottl et al., "Preparation and Photoactivation of Caged Fluorophores and Caged Proteins Using a New Class of Heterobifunctional, Photocleavable Cross-Linking Reagents," 1998 Bioconj Chem 9:143-151.
Vasey et al., "Phase I Clinical and Pharmacokinetic Study of PK1 [N-(2-Hydroxypropyl) methacrylamide Copolymer Doxorubicin] . . . ," 1999 Clin Cancer Res 5:83-94.
Capala et al., "Boronated Epidermal Growth Factor as a Potential Targeting Agent for Boron Neutron Capture Therapy of Brain Tumors," 1996 Bioconjugate Chem 7:7-15.
Press et al., "Expression of the HER-2/neu proto-oncogene in normal human adult and fetal tissues," 1990 Oncogene 5:953-62.
Pegram et al., Phase II study of intravenous recombinant humanized anti-p185 HER-2 Monoclonal Antibody (rhuMAb HER-2) plus Cisplatin in patients with HER-2/NEU overexpressing metastatic breast cancer, 1995 Am Soc Clin Oncol 14:106.
Park et al., "Anti-HER2 immunoliposomes for targeted therapy of human tumors," 1997 Cancer Lett 118:153-160.
Kirpotin et al., "Sterically Stabilized Anti-HER2 Immunoliposomes: Design and Targeting to Human Breast Cancer Cells in Vitro," 1997 Biochem 36:66.
Kjeldsen et al., "Preparation and Characterization of Monoclonal Antibodies Directed to the Tumor-associated O-linked Sialosyl-2- . . . ," 1988 Cancer Res 48:2214-2220.
Springer, et al., "Blood group Tn-active macromolecules from human carcinomas and erythrocytes: characterization of and specific reactivity with mono- and poly-clonal anti-Tn antibodies induced by various immunogens," 1988 Carbohydr Res 178:271-292.
Tjandra, et al., "Application of mammary serum antigen assay in the management of breast cancer: A preliminary report," 1988 J Surg 75:811-817.
Ishida et al., "Related Glycoproteins from Normal Secretory and Malignant Breast Cells," 1989 Tumor Biol 10:12-22.
Lan et al., "Isolation and properties of a human pancreatic adenocarcinoma-associated . . . ," 1985 Cancer Res 45:305-310.
Hanisch et al., "Structural studies on oncofetal carbohydrate antigens (Ca 19-9, Ca 50, and Ca 125) carried by O-linked sialyloligosaccharides on human amniotic mucins," 1988 Carbohydr Res 178:29-47.
Hinoda et al., "Immunochemical characterization of adenocarcinoma-associated antigen yh206," 1988 Cancer J 42:653-658.
Tuerk et al., "In vitro evolution of functional nucleic acids : high-affinity RNA ligands of HIV-1 proteins," 1993 Gene 137:33-9.
Binkley et al., "RNA ligands to human nerve growth factor ," 1995 Nuc Acids Res 23(16):3198-205.
Jellinek et al., "Inhibition of receptor binding by high-affinity RNA ligands to vascular endothelial growth factor," 1994 Biochem 33(34):10450-6.
Newton, D.L., et al., "Cytotoxic Ribonuclease Chimeras Tergeted Tumoricidal Activity in-vitro and in-vivo," Journal of Biological Chemistry, (1992) 267(27), pp. 19572-19578.
Suzuki M., et al., "Engineering receptor-mediated cytotoxicity into human ribonucleases . . . ," Nature Biotechnology, (1999) 17, pp. 265-270.
Mitchell et al., "Interfaces in Molecular Docking," Molec. Simul. (2004) 30, pp. 97-106.
Mohan C.G., et al, "The Crystal Structure of Eosinophil Cationic Protein in Complex with 2',5'-ADP at 2.0 A Resolution Reveals the Details of the Ribonucleolytic Active Site," Biochemistry, (2002) 41, pp. 12100-12106.

Moore J., et al., "Directed evolution of a para-nitrobenzyl esterase for aqueous-organic solvents," Nature Biotechnology, (1996) 14, pp. 458-467.
Mosimann S.C., et al., "X-ray Crystallographic Structure of Recombinant Eosinophil-derived Neurotoxin at 1.83 A Resolution," J. Mol. Biol., (1996) 260, pp. 540-552.
Narang S., "DNA Synthesis," Tetrahedron Report, (1983) 39(1), pp. 3-22.
Newton, D.L., et al., "Potent and specific antitumor effects of an anti-CD22-targeted cytotoxic ribonuclease . . . " Blood, (2001) 97(2), pp. 528-535.
Nguyen, D.M., et al., "Impact of Transfusion of Mediastinal Shed Blood on Serum Levels of Cardiac Enzymes," Ann. Thorac. Surg. 1996, 62, pp. 109-114.
Papageorgiou A.C., et al., "Molecular recognition of human angiogenin by placental ribonuclease inhibitor—an X-ray crystallographic study at 2.0 Å resolution," EMBO J., (1997) 16, pp. 5162-5177.
Potenza, N, et al., "Hybridase activity of human ribonuclease-1 revealed by a real-time fluorometric assay," Nucleic Acids Res, 2006, 34(10), pp. 2906-2913.
Pous J., et al, "Three-dimensional Structure of a Human Pancreatic Ribonuclease Variant, a Step Forward in the Design of Cytotoxic Ribonucleases," J Mol. Biol., (2000) 303, pp. 49-60.
Pous J., et al, "Three-dimensional structure of human RNase 1 AN7 at 1.9 A resolution," Acta Crystallogr D Biol Crystallogr., (2001) 57, pp. 498-505.
Raines, R.T., et al., "A New Remote Subsite in Ribonuclease A," J. Biol. Chem, 273, pp. 34134-34138 (1998).
Reddi, K.K., "Nature and Origin of Human Serum Ribonuclease" Biochem. Biophys. Res. Commun. 1975, 67(1), pp. 110-118.
Ribo, M., et al., "Heterogeneity in the Glycosylation Pattern of Human Pancreatic Ribonuclease," Biol. Chem. Hoppe-seyler, 375, pp. 357-363 (1994).
Roberts B., et al., "Directed evolution of a protein: Selection of potent . . . " Proc. Natl. Acad. Sci., (1992) 89, pp. 2429-2433.
Rosenberg H, et al, "Molecular cloning and characterization of a novel human ribonuclease (RNase k6): increasing diversity in the enlarging ribonuclease gene family," Nucleic Acids Research, (1994) 24, pp. 3507-3513.
Rybak S., et al., "Rational Immunotherapy With Ribonuclease Chimeras," Cell Biophysics, (1992) 21(1-3), pp. 121-138.
Rybak, S., et al., "Cytotoxic Potential of Ribonuclease and Ribonuclease Hybrid Proteins," Journal of Biological Chemistry, (1991) 266(31), pp. 21202-21207.
Scott J., et al., "Searching for peptide ligands with an Epitope library," Science, (1990) 249, pp. 386-390.
Shapiro, R., et al., "Analysis of the Interactions of Human Ribonuclease Inhibitor with Angiogenin and Ribonuclease A by Mutagenesis: Importance of Inhibitor Residues Inside versus Outside the C-terminal "Hot Spot"," J. Mol. Biol., 302, pp. 497-519 (2000).
Skerra, et al., "Engineered protein scaffolds for molecular recognition," J Mol Recognit. 2000, 13:167-87.
Smith G., "The progeny of sexual PCR," Nature, (1994) 370, pp. 324-325.
Sorrentino, S., et al., "Degradation of Double-Stranded RNA by Human Pancreatic Ribonuclease: Crucial Role of Noncatalytic BasicAmino Acid Residues," Biochemistry 42, pp. 10182-10190 (2003).
Stemmer W., "DNA shuffling by random fragmentation and reassembly . . . ," Proc. Natl. Acad. Sci., (1994) 91, pp. 10747-10751.
Stemmer W., "Rapid evolution of a protein in vitro by DNA shuffling," Nature, (1994) 370, pp. 389-391.
Stryer L., "Introduction of Proteins," Biochemistry, 2nd Edition,(1981) pp. 17-21.
Swaminathan G., et al, "Atomic Resolution (0.98 A) Structure of Eosinophil-Derived Neurotoxin," Biochemistry, (2002) 41, pp. 3341-3352.
Terzyan S.S., et al, J Mol. Biol., (1999) 285, pp. 205-214.
Trautwein, K. et al., "Site-directed mutagenesis of bovine pancreatic ribonuclease: lysine-41 and aspartate-121," FEBS Lett., 281, pp. 275-277 (1991).

(56) References Cited

OTHER PUBLICATIONS

Yamamura, t., et al., "Immunosuppressive and Anticancer Effect of a Mammalian Ribonuclease that Targets High-affinity Interleukin-2 receptors," European Journal of Surgery, (2002) 168(1), pp. 49-54.
Zhang J., et al, "Human RNase 7: a new cationic ribonuclease of the RNase A superfamily," Nucleic Acids Res., (2003) 31, pp. 602-607.
Zhang J., et al., "Directed evolution of a fucosidase from a galatosidase by DNA shuffling and screening," Proc. Natl. Acad. Sci., (1997) 94, pp. 4504-4509.
Zhao H., et al., "Optimization of DNA shuffling for high fidelity recombination," Nucleic Acids Research,(1997) 25(6), pp. 1307-1308.
Zhou, et al., "Selection of Antibiotic-Resistant Bacterial Mutants: Allelic Diversity among Fluoroquinolone-Resistant Mutations," 2000 JID 182:517-525.
Backer et al., 2004, "Adapter Protein for Site-Specific Conjugation of Payloads for Targeted Drug Delivery", Bioconjugate Chem., 15: 1021-1029.
Deonarain, M.P. et al., "Targeting enzymes for cancer therapy: Old Enzymes in New Roles." British Journal of Cancer, Nov. 1994 70(5):786-794.
Lavis et al., "Tuning the pKa of Flourescein to Optimize Binding Assays," 2007 Anal Chem, 79:6775-6782.
Wang, "An exact mathematical expression for describing competitive binding of two different ligands to a protein molecule", 1995 FEBS Lett 360: 111-114.
Roehrl et al., "A General Framework for Development and Data Analysis of Competitive High-Throughput Screens for Small-Molecule Inhibitors of Protein-Protein Interactions by Fluorescence Polarization," 2004 Biochem 43: 16056-16066.
Kelemen et al., "Hypersensitive substrate for ribonucleases", 1999 Nucl Acids Res, 27: 3696-3701.
Smith et al., "Potent Inhibition of Ribonuclease A by Oligo(vinylsulfonic Acid)", 2003 J Biol Chem 278:20934-30938.
Del Cardayre & Raines, "Structural Determinants of Enzymatic Processivity", 1994 Biochem 33:6031-6037.
Bal, H., et al, "Human pancreatic ribonuclease Deletion of the carboxyl-terminal EDST extension enhances ribonuclease activity and thermostability," Eur. J. Biochem., 245, pp. 465-469 (1997).
Ban et al., Proc. 8th Ann. Intl. Conf. Res. Comp. Mol.Biol., (2004) pp. 205-212.
Benito, A., et al., "Stabilization of human pancreatic ribonuclease through mutation at its N-terminal edge," Protein Eng., 15, pp. 887-893 (2002).
Boix E., et al., "Crystal Structure of Eosinophil Cationic Protein at 2.4 A Resolution," Biochemistry, (1999) 38, pp. 16794-16801.
Bosch, M., et al., "A Nuclear Localization Sequence Endows Human Pancreatic Ribonuclease with Cytotoxic Activity," Biochemistry, 43, pp. 2167-2177 (2004).
Bretscher, Leland, et al., "A Ribonuclease A variant with low catalytic activity but potent cytotoxic activity," J Biol. Chem., (2000) 275, 9893-9896.
Cadwell R.C., et al., "Randomization of Genes by PCR Mutagenesis," PCR Methods and Applications, (1992) 1(4), pp. 28-33.
Crameri A., et al., "Improved Green Flourescent Protein by Molecular Evolution," Nature Biotechnology, (1996)14, pp. 315-319.
Crameri A., et al., "Molecular evolution of an arsenate detoxification pathway by DNA shuffling," Nature Biotechnology, (1997) 15, pp. 436-438.
Curran, T.P., et al., "Alteration of the Enzymatic Specificity of Human Angiogenin by Site-Directed Mutagenesis," Biochemistry 32, pp. 2307-2313 (1993).
Cwirla S., et al., "Peptides onphage: A vast library of peptides for identifying ligands," Proc. Natl. Acad. Sci., (1990) 87, pp. 6378-6382.
Davis et al., Basic Methods in Molecular Biology. (1986).
De Lorenzo, C., "A Fully Human Antitumor ImmunoRNase Selective for ErbB-2-Positive Carcinomas," Cancer Res., (2004) 64, pp. 4870-4874.
Dermer, GB, "Another Anniversary for the War on Cancer," Bio/Technology. 1994, 12(March), p. 320.
Devlin J., et al., "Random Peptide Libraries: A source of specific protein Binding molecules," Science, (1990) 249, 404-406.
Dharap, S.S., et al., "Molecular Targeting of Drug Delivery Systems to Ovarian Cancer . . . " Journal of Controlled Release, (2003) 91, pp. 61-73.
Di Gaetano, G., et al., "Second generation antitumour human RNase: significance of its structural and functional features for the mechanism of antitumour action," Biochem. J., 358, pp. 241-247 (2001).
Dickson, K A, et al., "Compensating effects on the cytotoxicity of ribonuclease A variants," 2003 Archives Biochem and Biophysics, Acad Press, 415:172-177.
Eckert K, et al., "DNA Polymerase Fidelity and the Polymerase Chain Reaction," PCR Methods and Applications, (1991) 1(1), pp. 17-24.
Fisher, B.M., et al., "Coulombic Forces in Protein-RNA Interactions: Binding and Cleavage by Ribonuclease A and Variants at Lys7, Arg10, and Lys66," Biochemistry, 37, pp. 12121-12132 (1998).
Francis et al., Stability of protein pharmaceuticals: in vivo pathways of degradation and strategies for protein stabilization (Eds. Ahern., T. and Manning, M.C.) Plenum, N.Y., pp. 247-251 (1991).
Gaur, D. et al., "Interaction of human pancreatic ribonuclease with human ribonuclease inhibitor. Generation of inhibitor-resistant cytotoxic variants," J. Biol. Chem., 276:24978-24984 (2001).
Gaur, D., et al., "Role of aspartic acid 121 in human pancreatic ribonuclease catalysis," Mol. Cell. Biochem., 275, 95-101 (2005).
Gluzman Y., "SV40-transformed Simian Cells Support the Replication of Early SV40 Mutants," Cell, (1981) 23, pp. 175-182.
Gorman, C., et al. "The Hype and the Hope" Time. 1998, 151(19) pp. 40-44.
Gura, T., "Systems for Identifying New Drugs are Often Faulty," Science. 1997, 278(Nov. 7), pp. 1041-1042.
Gutte B., et al., "The synthesis of ribonuclease A," Journal of Biological Chemistry, (1971) 246(6), pp. 1922-1941.
Harder J., et al, "RNase 7, a Novel Innate Immune Defense Antimicrobial Protein of Healthy Human skin," J. Biol. Chem., (2002) 277, pp. 46779-46784.
Hursey, M., et al., "Specifically Targeting the CD22 Receptor of Human B-Cell Lymphomas With RNA . . . " Leukemia & Lymphoma, (2002) 43(5), pp. 953-959.
Ike Y., et al., "Solid phase synthesis of polynucleotides," Nucleic Acids Research, (1983) 11(2), pp. 477-488.
Itakura K., et al., "Chemical Synthesis . . . " Recombinant DNA, in Walton (ed.),Proceedings of 3rd Cleveland Symposium, (1981) pp. 273-289.
Itkaura K., et al., "Expression in E. coli of a Chemically Synthesized Gene for the hormone Somatostatin," Science, (1984) 198, pp. 1056-1063.
Itkaura K., et al., "Synthesis and Use of Synthetic Oligonucleotides," Ann. Rev. Biochem., (1984) 53, pp. 323-356.
Iyer S., et al, "Molecular Recognition of Human Eosinophil-derived Neurotoxin (RNase 2) by Placental Ribonuclease Inhibitor," J Mol. Biol., (2005) 347, pp. 637-655.
Jinno H., et al., "The Cytotoxicity of a Conjugate Composed of Human Epidermal Growth Factor," Anticancer Res., (2002) 22, pp. 4141-4146.
Jinno H., et al., "Epidermal Growth Factor Receptor-Dependent Cytotoxicity for Human Squamous Carcinoma Cell Lines . . . ," Life Sciences, (1996) 58(21), pp. 1901-1908.
Jinno U.H., et al., "Epidermal growth factor receptor-dependent cytotoxic effect by an EGF-ribonuclease conjugate . . . " Cancer Chemotherapy and Pharmacology, (1996) 38(4), pp. 303-308.
Klink ,T A, et al., "Conformational stability is a determinant of ribonuclease A cytotoxicity," 2000, J Biolog Chem, 275:17463-17467.
Kobe, et al., "Mechanism of ribonuclease inhibition by ribonuclease inhibitor protein based on the crystal structure of its complex with ribonuclease A," J Mol Biol, 1996, 264:1028-43.
Krasnykh V, et al., "Characterization of an Adenovirus Vector Containing a Heterologous Peptide Epitope in the HI Loop of the Fiber Knob," J Virology, (1998) 72, pp. 1844-1852.
Leland, P.A., et al., "Ribonuclease A Variants with Potent Cytotoxic Activity," Proc. Natl. Acad. Sci., 95, pp. 10407-10412 (1998).

(56) References Cited

OTHER PUBLICATIONS

Leonidas D.D., et al, "Binding of phosphase and pyrophosphate isons at the active site of human angiogenin as revealed by X-ray crystallography," Protein Sci., (2001) 10, pp. 1669-1676.

Leonidas D.D., et al, "The Three-dimensional Structure of Human RNase 4, Unliganded and Complexed with d(Up), Reveals the Basis for its Uridine Selectivity," J. Mol. Biol., (1999) 285, pp. 1209-1233.

Leung D., et al., "A Method for Random Mutagenesis of a defined DNa Segment using . . . ," Technique, (1989) 1(1), pp. 11-15.

Lin, M.C., "The Structural Roles of Amino Acid Residues Near the Carboxyl Terminus of Bovine Pancreatic Ribonuclease A," J. Biol. Chem., 245, pp. 6726-6731 (1970).

Mallorqui-Fernandez, G., et al., "Three-dimensional Crystal Structure of Human Eosinophil Cationic Protein (RNase 3) at 1.75 A Resolution," J. Mol. Biol., (2000) 300, pp. 1297-1307.

McGrath M., et al., "Immunotoxin Resistance in Multidrug Resistant Cells," Cancer Research, (2003) 63, pp. 72-79.

McKie, R., "Cancer Research Set Back a Decade," The Observer. Jun. 10, 2001, pp. 1-4.

McLane K, "Transplantation of a 17-amino acid a-helical DNA-binding domain into an antibody molecule confers sequence-dependent DNA recognition," Proc. Natl. Acad. Sci., (1995) 92, pp. 5214-5218.

Merlino, A., et al., "The importance of Dynamic Effects on the Enzyme Activity X-ray Structure and Molecular Dynamics of Onconase Mutants," J Biol Chem 2005, 280:17953-17960.

Futami J., et al., "Inhibition of cell growth by a fused protein of human ribonuclease 1 and human basic fibroblast growth factor" Protein Engineering, 12(11), pp. 1013-1018 (1999).

Laznicek, et al. "Pharmacokinetics and Distribution of Ribonuclease and its Monomethoxypoly(Ethylene Glycol) Derivatives in Rats" Pharmacological Research, vol. 28, No. 2, pp. 153-162 (1993).

Leland, P.A. et al., "Cancer Chemotherapy—Ribonucleases to the Rescue," Chem and Biology,8, pp. 405-413 (2001).

Matousek, et al. "Effect of hyaluronidase and PEG chain conjugation on the biologic and antitumor activity of RNase A" Journal of Controlled Release, vol. 94, No. 2-3, pp. 401-410 (2004).

Michaelis, et al. "Coupling of the antitumoral enzyme bovine seminal ribonuclease to polyethylene glycol chains increases its systemic efficacy in mice" Anti-Cancer Drugs, vol. 13, No. 2, , pp. 149-154 (2002).

Milton Harris J et al: "Effect of Pegylation on Pharmaceuticals" Nature Reviews. Drug Discovery, vol. 2, No. 3, pp. 214-221 (2003).

Newton, D.L., et al., "Cytotoxic Ribonuclease Chimeras Tergeted Tumoricidal Activity in-vitro and in-vivo," Journal of Biological Chemistry, 267(27), pp. 19572-19578 (1992).

Pouckova, et al. "Polymer-conjugated bovine pancreatic and seminal ribonucleases inhibit growth of human tumors in nude mice" Journal of Controlled Release, vol. 95, No. 1, pp. 83-92 (2004).

Psarras, K, et al., "Human pancreatic RNase1-human epidermal growth factor fusion: An entirely human immunotoxin analog with cytotoxic properties against squamous cell carcinomas," Protein Eng,11, pp. 1285-1292 (1998).

Zhang J., et al, "RNase 8, a Novel RNase A Superfamily Ribonuclease Expressed Uniquely in Placenta," Nucleic Acids Res., (2002) 30, pp. 1169-1175.

Matousek, et al. "Effect of hyaluronidase and PEG chain conjugation on the biologic and antitumor activity of RNase A" Journal of Controlled Release, vol. 94, No. 2-3, 2004, pp. 401-410.

Strong, Laura E, et al., "Human ribonuclease variants with broad anti-cancer activity," 2006, Am Assoc for Cancer Res Annual Mtg, 47, P514.

Piccoli, Renate et al., "A dimeric mutant of human pancreatic ribonuclease with selective cytotoxicity toward malignant cells," 1999, Pro Nat Acad Sci, 96, pp. 7768-7773.

Strong, L E et al., "408 Poster Human RNase 1 variants are effective anti-cancer agents," 2006, EP J Cancer Supp, Pergamon, Oxford, GB, 4, p. 125.

Matousek J, "Ribonucleases and their antitumor activity," 2001, Comp Biochem Physiology Tox Pharma, 129, pp. 175-191.

Rosenberg H F et al., "Eosinophils, Eosinophil Ribonucleases, and their Role in Host Defense Against Respiratory Virus Pathogens," 2001, J Leukocyte Bio, Fed Am Soc Exper Bio, 70, pp. 691-698.

Leland, P.A., et al., "Endowing Human Pancreatic Ribonuclease with Toxicity for Cancer Cells," Journal of Biological Chemistry, (2001) 276(46), pp. 43095-43102.

Zalipsky, "Functionalized Poly(ethylene glycol) for Preparation of Biologically Relevant Conjugates," Bioconjugate Chem 6, 150-165 (1995).

Rutkoski et al., "Disruption of Shape-Complementarity Markers to Create Cytotoxic Variants of Ribonucleases A". J Molecular Biology 2005, 354(1): 41-54.

Leonidas et al., "Refined Crystal Structures of Native Human Angiogenin and Two Active Site Variants: Implications for the Unique Functional Properties of an Enzyme Involved in Neovascularisation during Tumour Growth." J. Mol. Biol. 1999, 285:1209-1233.

Matousek et al. "PEG chains increase aspermatogenic and antitumor activity of RNase A and BS-RNase enzymes" Journal of Controlled Release 82 (2002) 29-37.

Monfardini et al., "A Branched Monomethoxypoly(ethylene glycol) for Protein Modification" Bioconjugate Chem. 1995, 6(1): 62-69.

Terzyan S.S., "The Three-dimensional Structure of Human RNase 4, Unliganded and Complexed with d(Up), Reveals the Basis for its Uridine Selectivity", et al, J Mol. Biol., (1999) 285, pp. 205-214.

\* cited by examiner

FIGURE 1

| AA# | RNase 1 | RNase 2 | RNase 3 | RNase 4 | RNase 5 | RNase 6 | RNase 7 | RNase 8 |
|---|---|---|---|---|---|---|---|---|
| | - | K + | R + | | | W | K | K |
| | - | P + | P + | | | P | P | P |
| 1 | K + | P + | P + | Q 0 (a1) | Q + | K | K | K |
| 2 | E + | Q + | Q + | D 0 (a1) | D + | R | G | D |
| | - | F + (dis) | F + | - | N 0 (a1) | L | M | M |
| 3 | S + | T + | T + | G 0 (a1) | S 0 (a1) | T | T | T |
| 4 | R 0 (a1) | W + (a1, RI) | R 0 (a1) | M 0 (a1) | R 0 (a1, RI, P2) | K | S | S |
| 5 | A 0 (a1) | A 0 (a1) | A 0 (a1) | Y 0 (a1) | Y 0 (a1) | A | S | S |
| 6 | K 0 (a1) | Q 0 (a1) | Q 0 (a1) | Q 0 (a1) | T 0 (a1) | H | Q | Q |
| 7 | K 0 (a1) | W — (a1, P2) | W 0 (a1) | R 0 (a1) | H + (a1, RI) | W | W | W |
| 8 | F 0 (a1) | F 0 (a1) | F 0 (a1) | F 0 (a1) | F 0 (a1) | F | F | F |
| 9 | Q 0 (a1) | E 0 (a1) | A 0 (a1) | L 0 (a1) | L 0 (a1) | E | K | K |
| 10 | R 0 (a1) | T — (a1, P2) | I 0 (a1) | R 0 (a1) | T 0 (a1) | I | I | T |
| 11 | Q 0 (a1) | Q 0 (a1) | Q — (P1, a1) | Q — (a1, P1) | Q 0 (a1, RI, P1) | Q | Q | Q |
| 12 | H — (P1, a1) | H — (P1, a1) | H — (P1, a1) | H — (P1, a1) | H — (P1, a1) | H— (P1) | H— (P1) | H— (P1) |
| 13 | M + | I + | I | V + | Y + | I | M | V |
| 14 | D + | N + | S | H + | D + | Q | Q | Q |
| 15 | S + | M + | L | P + | A + | P | P | P |
| 16 | D + | T + | N | E + | K + | S | S | S |

FIGURE 1 (CONT.)

| | | | | | | | | |
|---|---|---|---|---|---|---|---|---|
| 17 | S + | S + | P | E + | - | P | P | P |
| 18 | S + | Q + | P | Y + | P + | L | Q | Q |
| 19 | P + | Q + (RI, dis) | R | - | Q + | Q | A | A |
| 20 | S + | - | - | G + | G + | - | - | - |
| 21 | S + | - | - | G + | R + | - | - | - |
| 22 | S + | - | - | S + | D + | - | - | - |
| 23 | S + | - | - | D 0 (a2) | D 0 (a2) | - | - | - |
| 24 | T + | - | - | R 0 (a2) | R + (a2, RI) | - | - | - |
| 25 | Y 0 (a2) | - | - | Y 0 (a2) | Y 0 (a2) | - | - | - |
| 26 | C − (a2, disulf) | C −−− (a2, disulf) | C −−− (disulf, a2) | C −−− (a2, disulf) | C −−− (a2, disulf) | C | C | C |
| 27 | N 0 (a2) | T 0 (a2) | T 0 (a2) | N 0 (a2) | E 0 (a2) | N | N | N |
| 28 | Q 0 (a2) | N + (a2, RI, dis) | I 0 (a2) | L 0 (a2) | S 0 (a2) | R | S | S |
| 29 | M 0 (a2) | A 0 (a2) | A 0 (a2) | M 0 (a2) | I 0 (a2) | A | A | A |
| 30 | M 0 (a2) | M 0 (a2) | M 0 (a2) | M 0 (a2) | M 0 (a2) | M | M | M |
| 31 | R + (a2, RI) | Q 0 (a2) | R 0 (a2) | Q 0 (a2) | R + (a2, RI) | S | K | S |
| 32 | R + (a2, RI) | V 0 (a2) | A 0 (a2) | R 0 (a2) | R+ (a2, RI) | G | N | I |
| 33 | R + | I 0 (a2, dis) | I 0 (a2) | R + | R + | I | I | I |
| 34 | N + | N 0 (a2) | N 0 (a2) | K + | G + | N | N | N |
| 35 | M + | N + (a2, RI, dis) | N + | M + | L + | N | K | K |
| 36 | T + | Y 0 (a2) | Y + | T + | T + | Y | H | Y |
| 37 | Q + (RI) | Q + (a2, RI) | R 0 (P-1) | L + | - | T | T | T |

FIGURE 1 (CONT.)

| | | | | | | | |
|---|---|---|---|---|---|---|---|
| 38 | G + (RI) | R + (RI) | W + | Y + | S + (RI) | Q | K | E |
| 39 | R + | R 0 (P-1, RI) | R + | H + | P + (RI) | H | R | R |
| 40 | C— (disulf) | C— (disulf) | C— (disulf) | C— (disulf) | C— (disulf) | C | C | C |
| 41 | K— (enz) | K— (enz, P1) | K— (P1) | K— (enz, P1) | K— (enz, P1, RI) | K | K | K |
| 42 | P 0 | N 0 (P-1, RI) | N + | R | D + (RI) | H | D | D |
| 43 | V 0 (b1) | Q — (P-1) | Q 0 (b1) | F 0 (b1) | I — (b1, B1) | Q | L | L |
| 44 | N 0 (b1) | N 0 (b1) | N 0 (b1) | N 0 (b1) | N— (b1, B1) | N | N | N |
| 45 | T 0 (b1) | T (b1, B1) | T— (b1, B1) | T 0 (b1) | T— (b1, B1) | T | T | T |
| 46 | F 0 (b1) | F 0 (b1) | F 0 (b1) | F 0 (b1) | F 0 (b1) | F | F | F |
| 47 | V 0 (b1) | L 0 (b1) | L 0 (b1) | I 0 (b1) | I 0 (b1) | L | L | L |
| 48 | H + | L + | R + | H + | H + | H | H | H |
| 49 | E+ | T + | T + | E + | G + | D | E | E |
| 50 | P+ | T | T + | D + | N | S | P | P |
| 51 | L 0 (a3) | F 0 (a3) | F 0 (a3) | I 0 (a3) | K 0 (a3) | F | F | F |
| 52 | V 0 (a3) | A 0 (a3) | A 0 (a3) | W 0 (a3) | R 0 (a3) | Q | S | S |
| 53 | D 0 (a3) | N 0 (a3) | N 0 (a3) | N 0 (a3) | S 0 (a3) | N | S | S |
| 54 | V 0 (a3) | V 0 (a3) | V 0 (a3) | I 0 (a3) | I 0 (a3) | V | V | V |
| 55 | Q 0 (a3) | V 0 (a3) | V 0 (a3) | R 0 (a3) | K 0 (a3) | A | A | A |
| 56 | N 0 (a3) | N + (a3, dis) | N 0 (a3) | S 0 (a3) | A 0 (a3) | A | A | I |

FIGURE 1 (CONT.)

| 57 | V 0 (a3) | V 0 (a3) | V + | I 0 (a3) | I 0 (a3) | V | T | T |
|---|---|---|---|---|---|---|---|---|
| 58 | C — (disulf) | C — (disulf, a3) | C — (disulf) | C — (disulf, a3) | C — (disulf, a3) | C | C | C |
| 59 | F 0 (a3) | G 0 (a3) | G | S + | E 0 (rec) | D | Q | Q |
| 60 | Q + | N + | N | T + | N 0 (rec) | L | T | T |
| 61 | E 0 (b2) | P + | Q | T + | K 0 (rec) | L | P | P |
| 62 | K 0 (b2) | N + | S | N + | N 0 (rec, b2) | S | K | N |
| 63 | V 0 (b2) | M + | I | I + | G 0 (rec, b2) | I | I | I |
| 64 | T 0 (b2) | T + | R | Q + | N 0 (rec, b2) | V | A | A |
| 65 | C — (disulf) | C — (disulf) | C — (disulf) | C — (disulf) | P 0 (rec, b2) | C | C | C |
| 66 | K + | P + | P | K + | H 0 (rec, b2) | K | K | K |
| 67 | N + (RI) | S 0 (P0, RI, dis) | H | N + | R 0 (b2) | N | N | N |
| 68 | G + | N + (RI) | N | G + | E 0 (rec, RI) | R | G | S |
| 69 | Q + | K + | R | K + | N 0 (rec) | R | D | C |
| 70 | G + | T + | T | M + | L 0 (b3) | - | - | - |
|  | - | R 0 (B2, RI, dis) | L | - | - | - | - | - |
|  | - | K + | N | - | - | H | K | K |

FIGURE 1 (CONT.)

| | | | | | | | | |
|---|---|---|---|---|---|---|---|---|
| 71 | N + | N 0 (B2, RI) | N — (B2) | N + | R 0 (b3) | N | N | N |
| 72 | C — (b3, disulf) | C — (b2, disulf) | C — (disulf, b2) | C — (b2, disulf) | I 0 (b3) | C | C | C |
| 73 | Y 0 (b3) | H 0 (b2) | H 0 (b2) | H 0 (b2) | S 0 (b3) | H | H | H |
| 74 | K 0 (b3) | H 0 (b2) | R 0 (b2) | - | K + | Q | Q | Q |
| 75 | S+ | S + | S + | - | S + | S | S | S |
| 76 | N+ | G + | R + | E 0 (b2) | S + | S | H | H |
| 77 | S+ | S + | F + | G 0 (b2) | - | K | G | G |
| 78 | S + | Q + | R + | V 0 (b2) | - | P | A | P |
| 79 | M 0 (b4) | V 0 (b3) | V 0 (b3) | V 0 (b2) | F 0 (b4) | V | V | M |
| 80 | H 0 (b4) | P 0 (b3) | P 0 (b3) | K 0 (b2) | Q 0 (b4) | N | S | S |
| 81 | I 0 (b4) | L 0 (b3) | L 0 (b3) | V 0 (b2) | V 0 (b4) | M | L | L |
| 82 | T 0 (b4) | I 0 (b3) | L 0 (b3) | T 0 (b2) | T 0 (b4) | T | T | T |
| 83 | D 0 (b4) | H — (B1) | H 0 (b3) | D — (b2, B1) | T — (b4, B1) | D | M | M |
| 84 | C — (b4, disulf) | C — (disulf, b3) | C — (disulf) | C — (disulf) | C — (disulf, b4) | C | C | G |
| 85 | R 0 (b4) | N + (b3, RI) | D 0 (b3) | R 0 (b2) | K 0 (b4) | R | K | E |
| 86 | L 0 (b4) | L + (b3, RI) | L 0 (b3) | D 0 (b2) | L 0 (b4) | L | L | L |
| 87 | T + | T + (b3, RI) | I + | T + | H + (b4, RI) | T | T | T |
| 88 | N + | T + (b3, RI) | N + | G + | G + (RI) | S | S | S |
| 89 | G + | P + (RI) | P + | S + | G+ (RI) | G | G | G |

FIGURE 1 (CONT.)

| | | | | | | | | |
|---|---|---|---|---|---|---|---|---|
| 90 | S + | S + | G + | S + | S + (RI) | - | - | - |
| 91 | R + | P + | A + | R + | P + (RI) | - | - | - |
| | - | Q + | Q + | - | - | - | - | - |
| | - | N + | N + | - | - | K | K | K |
| 92 | Y + | I + (RI) | I + | A + | W + (RI) | Y | H | Y |
| 93 | P + | S + (RI) | S + | P + | P + | P | P | P |
| 94 | N + | N + | N + | N + | P + | Q | N | N |
| 95 | C — (disulf) | C — (disulf) | C — (disulf) | C — (disulf) | C — (disulf) | C | C | C |
| 96 | A 0 | R 0 (b4) | R + | R + | Q + (b5, RI) | R | R | R |
| 97 | Y 0 (b5) | Y 0 (b4) | Y 0 (b4) | Y 0 (b3) | Y 0 (b5) | Y | Y | Y |
| 98 | R 0 (b5) | A 0 (b4) | A 0 (b4) | R 0 (b3) | R + (b5, RI) | S | K | K |
| 99 | T 0 (b5) | Q 0 (b4) | D 0 (b4) | A 0 (b3) | A 0 (b5) | A | E | E |
| 100 | S 0 (b5) | T 0 (b4) | R 0 (b4) | I 0 (b3) | T 0 (b5) | A | K | K |
| 101 | P 0 (b5) | P 0 (b4) | P 0 (b4) | A 0 (b3) | A 0 (b5) | A | R | H |
| 102 | K 0 (b5) | A 0 (b4) | G 0 (b4) | S 0 (b3) | G 0 (b5) | Q | Q | L |
| 103 | E 0 (b5) | N 0 (b4) | R 0 (b4) | T 0 (b3) | F 0 (b5) | Y | N | N |
| 104 | R0 (b5) | M 0 (b4) | R 0 (b4) | R — (b3, B1) | R 0 (b5) | K | K | T |
| 105 | H + | F + | F + | R — (b3, B1) | N + | F | S | P |
| 106 | I 0 (b6) | Y 0 (b5) | Y 0 (b5) | V 0 (b3) | V + | F | Y | Y |
| 107 | I 0 (b6) | I 0 (b5) | V 0 (b5) | V 0 (b3) | V 0 (b6) | I | V | I |
| 108 | V 0 (b6) | V 0 (b5) | V 0 (b5) | I 0 (b3) | V0 (b6) | V | V | V |

FIGURE 1 (CONT.)

| | | | | | | | |
|---|---|---|---|---|---|---|---|
| 109 | A 0 (b6) | A 0 (b5) | A 0 (b5) | A 0 (b3) | A + (b6, RI) | A | A | A |
| 110 | C— (disulf, b6) | C— (disulf, b5) | C— (disulf, b5) | C— (disulf, b3) | C— (disulf, b6) | C | C | C |
| 111 | E 0 (b6) | D—(B2, RI, b5) | D 0 (b5) | E 0 (b3) | E — (b6, RI, B2) | D | K | D |
| 112 | G + | N 0 (b5) | N— (B2, b5) | G + | N + | P | P | P |
| 113 | S + | R + | R + | N + | G + | P | P | P |
| | - | D + | D + | - | - | - | - | - |
| | - | Q + | P + | - | - | Q | Q | Q |
| | - | R + | R + | - | - | K | K | Q |
| | - | R + | - | - | - | S | K | G |
| | - | D + | D + | - | - | D | D | D |
| | - | P + | S + | - | - | P | S | P |
| | - | P + | P + | - | - | P | Q | G |
| | - | Q + | R + | - | - | - | Q | - |
| | - | Y + | Y + | - | - | Y | F | Y |
| 114 | P + | P + | P + | P + | - | K | H | P |
| 115 | Y + | V 0 (b6) | V 0 (b6) | Q + | - | L | L | L |
| 116 | V 0 (b7) | V 0 (b6) | V 0 (b6) | V 0 (b4) | L 0 (b7) | V | V | V |
| 117 | P 0 (b7) | P 0 (b6) | P 0 (b6) | P 0 (b4) | P 0 (b7) | P | P | P |
| 118 | V 0 (b7) | V + (b6, RI) | V 0 (b6) | V 0 (b4) | V 0 (b7) | V | V | V |
| 119 | H — (P1, b7) | H — (P1, RI, b6) | H— (P1, B2, b6) | H — (P1, b4) | H — (P1, b7) | H | H | H |
| 120 | F 0 (b7) | L — (b6, B1) | L— (B1, b6) | F 0 (b4) | L — (b7, B1) | L | L | L |
| 121 | D 0 (b7) | D 0 (b6) | D 0 (b6) | D 0 (b4) | D + | D | D | D |
| 122 | A 0 (b7) | R 0 (b6) | T 0 (b6) | G — (b4, P1) | Q + (a, RI) | S | R | K |

FIGURE 1 (CONT.)

| | | | | | | | |
|---|---|---|---|---|---|---|---|
| 123 | S 0 (b7) | I — (b6, B1) | T — (B1, b6) | - | S 0 (a) | I | V | V |
| 124 | V 0 (b7) | I + | I 0 (b6) | - | I 0 (a) | L | L | V |
| 125 | E 0 (b7) | - | - | - | F 0 (a) | - | - | - |
| 126 | D 0 (b7) | - | - | - | R + | - | - | - |
| 127 | S + | - | - | - | R + | - | - | - |
| 128 | T + | - | - | - | P + | - | - | - |

FIGURE 10
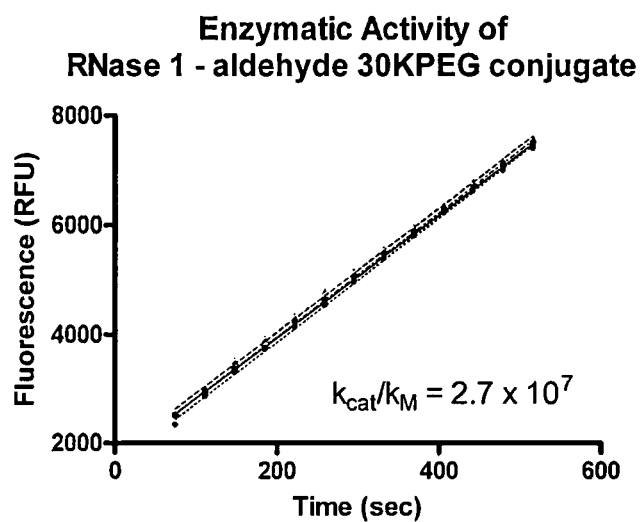
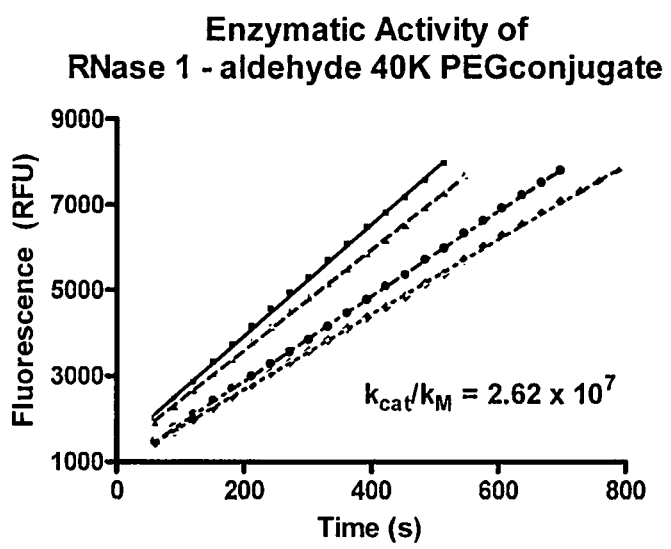

FIGURE 11
Efficacy of RNase 1 - aldehyde 30K PEG conjugate against the A549 cell line
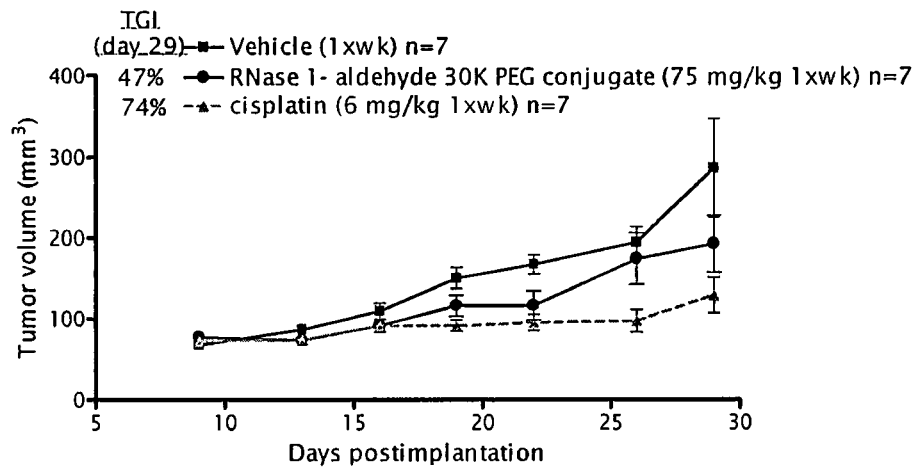
Toxicity of agents reflected by changes in body weight
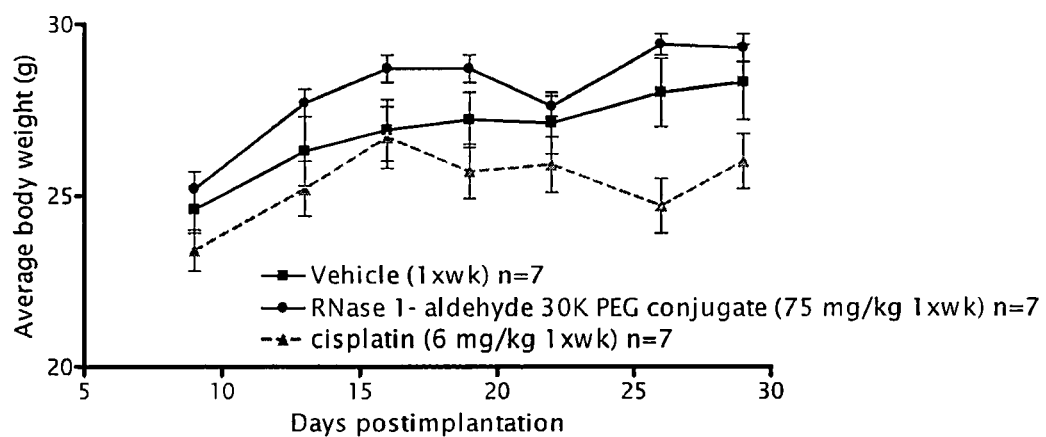

FIGURE 12
Efficacy of RNase 1 - aldehyde 40K PEGconjugate against the A549 cell line
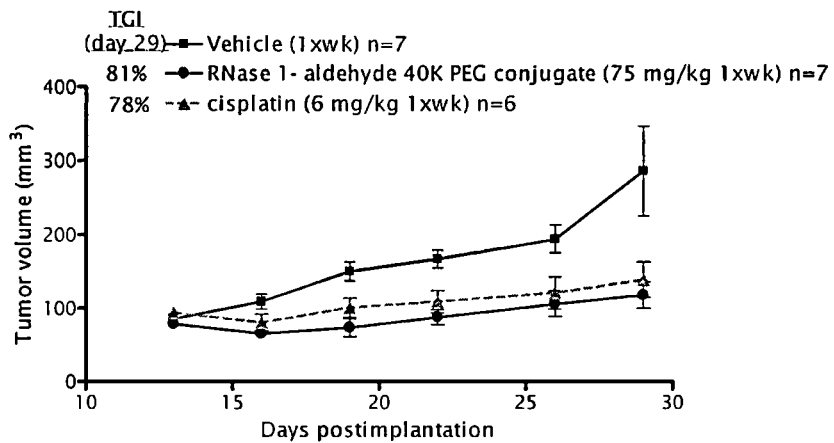
Toxicity of agents reflected by changes in body weight
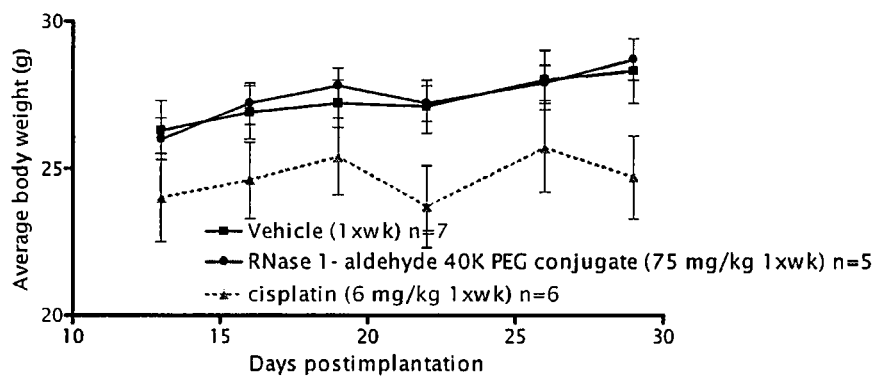

FIGURE 13
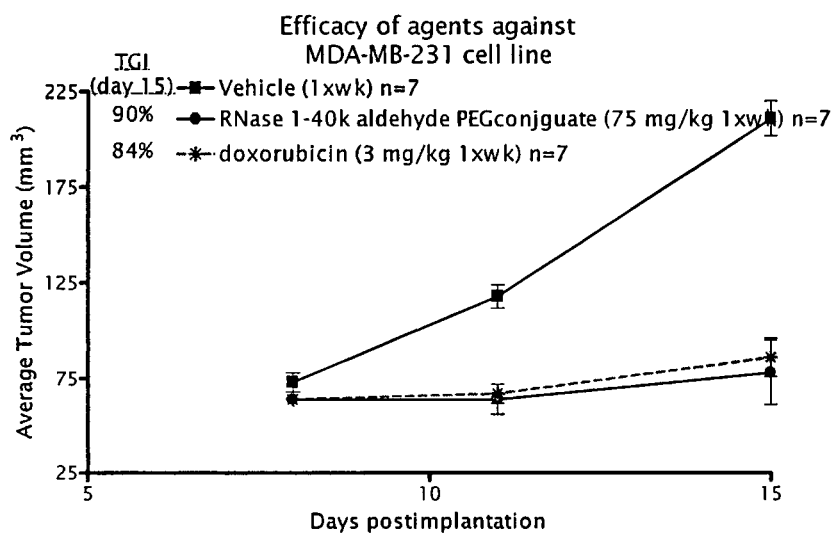
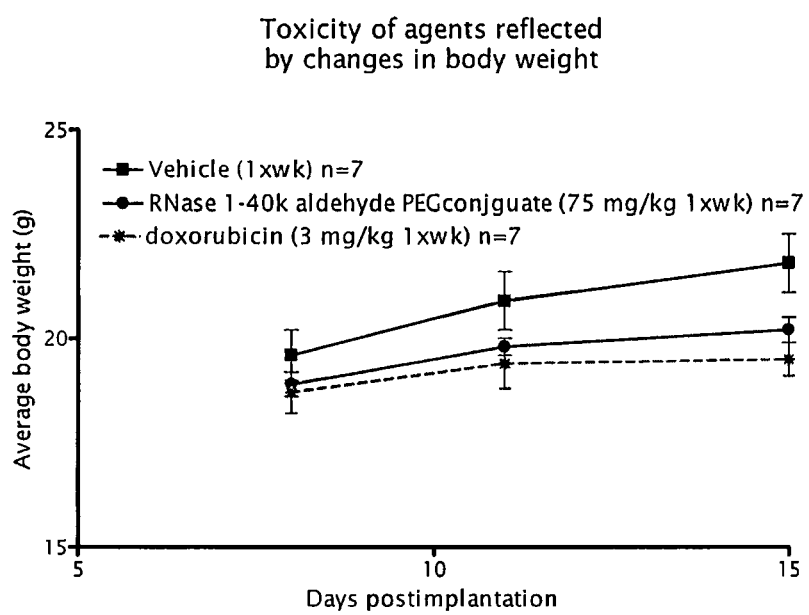

MODIFIED RIBONUCLEASES

The present invention claims priority to U.S. Provisional Patent Application Ser. No. 60/816,179, filed Jun. 23, 2006, hereby incorporated by reference in its entirety.

FIELD OF THE INVENTION

The present invention relates generally to conjugates of ribonucleases (e.g., human ribonucleases) and water-soluble polymers, compositions comprising the conjugates and methods of using the same. In particular, the present invention provides conjugates of ribonucleases (e.g., human ribonucleases) and one or more water-soluble polymer compositions (e.g., to increase serum half-life and a pharmacokinetic profile, in vivo biological activity, stability, and/or reduce host immune response to the protein in vivo) as well as methods of using the conjugates in the therapy, treatment, and/or prevention of disease (e.g., cancer).

BACKGROUND OF THE INVENTION

"Cancer" generally refers to one of a group of more than 100 diseases caused by the uncontrolled, abnormal growth of cells that can spread to adjoining tissues or other parts of the body. Cancer cells can form a solid tumor, in which the cancer cells are massed together, or exist as dispersed cells, as in leukemia. Normal cells generally divide until maturation is attained and then only as necessary for replacement of damaged or dead cells. Cancer cells are often referred to as "malignant", because they divide endlessly, eventually crowding out nearby cells and spreading to other parts of the body. The tendency of cancer cells to spread from one organ to another or from one part of the body to another distinguishes them from benign tumor cells, which overgrow but do not spread to other organs or parts of the body. Malignant cancer cells eventually metastasize and spread to other parts of the body via the bloodstream or lymphatic system, where they can multiply and form new tumors. This sort of tumor progression makes cancer a deadly disease. Although there have been great improvements in the diagnosis and treatment of cancer, many people die from cancer each year, and their deaths are typically due to metastases and cancers that are resistant to conventional therapies.

Most drug-mediated cancer therapies rely on chemotherapeutic agents (e.g., cytotoxic agents) selective for dividing cells. However, certain cancers do not respond to existing chemotherapeutic agents. Thus, there exists great need and hope, both within the medical community and among the general population, for the development of novel chemotherapeutic agents for the treatment of cancer.

SUMMARY OF THE INVENTION

The present invention relates to the conjugation of ribonucleases (e.g., human ribonucleases (hRNases)) to water-soluble polymers to improve their clinical properties in terms of their pharmacokinetics, pharmacodynamics, and/or reduced immunogenicity. In preferred embodiments, the present invention relates to the conjugation of ribonucleases (e.g., hRNases) to poly(alkylene oxides) (e.g., polyethylene glycol (PEG)). The present invention is not limited by the type of hRNase utilized. Indeed, any hRNase can be used in the compositions and methods of the present invention including, but not limited to, human pancreatic ribonuclease (e.g., hRNase 1, hRNase 2, hRNase 3, hRNase 4, hRNase 5, hRNase 6, hRNase 7, hRNase 8).

In some embodiments, the present invention provides for polymer conjugation of hRNase to increase its circulating half-life in vivo while retaining ribonuleolytic activity or other desired function (e.g., cancer cell killing). hRNase so modified may thus be used to treat (e.g., therapeutically or prophylacticly) cancer (e.g., at a reduced and/or less frequent dosage than an unmodified hRNase).

In some embodiments, the present invention provides for polymer conjugation of bovine ribonucleases (e.g., ribonuclease A) to increase its circulating half-life in vivo while retaining ribonuleolytic activity or other desired function (e.g., cancer cell killing). In some embodiments, ribonuclease A is conjugated to a water-soluble polymer in a region of the protein involved in evasion from ribonuclease inhibitor (RI). In some preferred embodiments, ribonuclease A is conjugated to a water-soluble polymer in a region of the protein that is not involved in evasion from RI (e.g., a region that has no impact on binding of ribonuclease A to the RI). Thus, although an understanding of the mechanism is not necessary to practice the present invention and the present invention is not limited to any particular mechanism of action, in some embodiments, conjugation of a water soluble polymer to ribonuclease A possess biological activity (e.g., cancer cell killing) even though the conjugation does not assist the ribonuclease from evading the RI.

In addition to increasing circulating half-life while retaining biological activity (e.g., ribonuleolytic activity and/or cancer cell killing potential), other advantages obtained by polymer conjugation include, but are not limited to, decreased antibody binding, increased efficacy (e.g., for killing or prohibiting growth of cancer cells), decreased immunogenicity, and reduced binding to circulatory system surfaces.

In some embodiments, the present invention provides water-soluble polymers (e.g., polyethylene glycol (PEG)) conjugated to a ribonuclease (e.g., hRNase), such that at least a portion of the ribonuleolytic activity of ribonuclease (e.g., hRNase) is retained. In some embodiments, at least 1%, at least 5%, at least 10%, at least 20%, at least 30%, at least 40%, at least 50%, at least 60%, at least 70%, at least 75%, at least 80%, at least 85%, at least 90%, at least 95%, at least 97% or more of RNase activity is retained post conjugation to the water-soluble polymer compared to un-conjugated hRNase. In some embodiments, hRNase may retain more (e.g., greater than 97%) or less (e.g., less than 1%) ribonucleolytic activity after conjugation to a water-soluble polymer. In some embodiments, a conjugate of the present invention retains at least one desired property (e.g., the ability to kill cancer cells (e.g., in the presence or absence of ribonucleolytic activity) compared to treatment in the absence of the conjugate).

The present invention is not limited by the route or type of administration of a ribonuclease (e.g., hRNase) conjugate of the present invention. Indeed, a variety of routes of administration are contemplated to be useful including, but not limited to, ophthalmic, oral, transdermal and/or topical, nasal, into the lungs (e.g., via an inhalant), mucosal (e.g., vaginal or nasal mucosa, rectal, via the ear, by injection (e.g., intravenously, subcutaneously, intratumorally, intraperitoneally, directly into a tumor, etc.) and the like. In some embodiments, one or more other chemotherapeutic agents (e.g., anti-cancer agents) are co-administered with a hRNase conjugate (e.g., PEG-hRNase conjugate) of the present invention. The present invention is not limited to the type of chemotherapeutic agent co-administered. Indeed, a variety of chemotherapeutic agents are contemplated to be useful for co-administration with a composition of the present invention including, but not limited to, chemicals, peptides, proteins and lipopeptides (e.g., that may, upon contacting a cancer cell in a host, kill the cell by any of a variety of techniques (e.g., induce apoptosis) without damaging host cells or tissues or eliciting a harmful host response.

The present invention is not limited by the type of water-soluble polymer to which the ribonuclease (e.g., hRNase) is conjugated. For example, water-soluble polymers include, but are not limited to, poly(alkylene oxides), polyoxyethylated polyols and poly(vinyl alcohols). Poly(alkylene oxides) include, but are not limited to, PEGs, poloxamers and poloxamines. The present invention is not limited by the type of conjugation utilized (e.g., to connect a hRNase molecule to one or more water-soluble polymers (e.g. PEG)). In some embodiments, a poly(alkylene oxide) is conjugated to a free amino group via an amide linkage (e.g., formed from an active ester (e.g., the N-hydroxysuccinimide ester)) of the poly(alkylene oxide). In some embodiments, an ester linkage remains in the conjugate after conjugation. In some embodiments, linkage occurs through a lysine residue present in the ribonuclease (e.g., hRNase) molecule. In some embodiments, conjugation occurs through a short-acting, degradable linkage. The present invention is not limited by the type of degradable linkage utilized. Indeed, a variety of linkages are contemplated to be useful in the present invention including, but not limited to, physiologically cleavable linkages including ester, carbonate ester, carbamate, sulfate, phosphate, acyloxyalkyl ether, acetal, and ketal linkages. In some embodiments, hRNase is conjugated to PEG utilizing any of the methods, reagents and/or linkages described in U.S. Pat. Nos. 4,424,311; 5,672,662; 6,515,100; 6,664,331; 6,737,505; 6,894,025; 6,864,350; 6,864,327; 6,610,281; 6,541,543; 6,515,100; 6,448,369; 6,437,025; 6,432,397; 6,362,276; 6,362,254; 6,348,558; 6,214,966; 5,990,237; 5,932,462; 5,900,461; 5,739,208; 5,446,090 and 6,828,401; and WO 02/02630 and WO 03/031581, each of which is herein incorporated by reference in its entirety. In some embodiments, a conjugate of the present invention is produced by a third party (e.g., NEKTAR, San Carlos, Calif.). In some embodiments, the conjugate comprises a cleavable linkage present in the linkage between the polymer and ribonuclease (e.g., hRNase) (e.g., such that when cleaved, no portion of the polymer or linkage remains on the hRNase molecule). In some embodiments, the conjugate comprises a cleavable linkage present in the polymer itself (e.g., such that when cleaved, a small portion of the polymer or linkage remains on the hRNase molecule). In some embodiments, the PEG-ribonuclease conjugate is purified after conjugation. The present invention is not limited by the type of purification process utilized. Indeed, a variety of processes may be utilized including, but not limited to, ion exchange chromatography, hydrophobic interaction chromatography, size exclusion chromatography, and other methods well known in the art. The present invention is not limited by the type of PEG molecule utilized. Indeed, a variety of PEG molecules are contemplated to be useful for conjugation to a ribonuclease (e.g., hRNase) molecule of the present invention including, but not limited to, linear or straight chained PEG or branched PEG and may have a molecular weight of between about 1 kDa and about 500 kDa (e.g., in some embodiments, is between 10-50 kDa), although a PEG molecule conjugated to a hRNase molecule may be larger (e.g., greater than 500 kDa) or smaller (e.g., less than 1 kDa).

The present invention also provides a method for the prophylactic or therapeutic treatment of a cancer in a subject (e.g., a mammal) by administering to the subject an effective amount of a composition (e.g., pharmaceutical preparation) comprising a ribonuclease conjugate (e,g, PEG-hRNase conjugate) of the present invention (e.g., comprising a pharmaceutically acceptable carrier). The present invention is not limited by the type of cancer treated. Indeed, a variety of cancers are contemplated to be treatable (e.g., killed or growth inhibited) by a ribonucleolytic conjugate of the present invention including, but not limited to, acute lymphocytic leukemia, acute myelocytic leukemia, acoustic neuroma, adenocarcinoma, angiosarcoma, astrocytoma, basal cell carcinoma, bile duct carcinoma, bladder carcinoma, bone originated tumor, bone sarcoma, brain tumor, breast cancer, bronchogenic carcinoma, carcinoma, cervical cancer, chondrosarcoma, chordoma, choriocarcinoma, chronic lymphocytic leukemia, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, glioma, heavy chain disease, hemangioblastoma, hepatic carcinoma, hodgkin's lymphoma, leiomyosarcoma, leukemia, liposarcoma, lung carcinoma, lymphangioendotheliosarcoma, lymphangiosarcoma, medullary carcinoma, medulloblastoma, melanoma, meningioma, mesothelioma, multiple myeloma, myxosarcoma, neuroblastoma, non-Hodgkin's lymphoma, pancreatic cancer, oligodendroglioma, osteogenic sarcoma, ovarian cancer, pancreatic carcinoma, papillary carcinoma, papillary adenocarcinoma, pinealoma, polycythemia vera, acute promyelocytic leukemia, prostate cancer, rectal cancer, renal cell carcinoma, retinoblastoma, rhabdomyosarcoma, sarcoma, sebaceous gland carcinoma, seminoma, small cell lung carcinoma, squamous cell carcinoma, stomach carcinoma, synovioma, sweat gland carcinoma, testicular tumor, uterus carcinoma, Waldenstrom's macroglobulinemia, and Wilms' tumor.

In some embodiments, the present invention provides a composition comprising polyethylene glycol (PEG) conjugated to hRNase or hRNase analogue (e.g., non-naturally occurring hRNase) wherein the conjugate comprises a degradable linkage (e.g., an ester linkage), wherein at least a portion of the nucleolytic activity of the hRNase or hRNase analogue is retained. In some embodiments, the hRNase or hRNase analogue conjugated to polyethylene glycol through a degradable linkage has a longer in-vivo half-life than non-conjugated hRNase or hRNase analogue (e.g., due to decreased affinity between the hRNase-PEG conjugate and ribonuclease inhibitor (RI)). In some embodiments, the hRNase or hRNase analogue is capable of degrading RNA (e.g., via enzymatic activity of the ribonuclease). In some embodiments, conjugating the hRNase or hRNase analogue to the polyethylene glycol permits a greater serum concentration of hRNase or hRNase analogue than is achievable for non-conjugated hRNase or hRNase analogue. In some embodiments, the hRNase or hRNase analogue is a recombinant hRNase or hRNase analogue. In some embodiments, the hRNase is naturally derived. In some embodiments, the recombinant hRNase possesses a terminal cysteine. The present invention is not limited by the number of water-soluble polymers (e.g., PEGs) attached to a hRNase molecule. In some embodiments, a single water-soluble polymer is attached to a hRNase molecule. In some embodiments, two, three, four, five or more water-soluble polymers (e.g., PEGs) are attached to a hRNase molecule. In some embodiments, the conjugate comprises from one to about four polymer molecules per molecule of hRNase or hRNase analogue. In some embodiments, the PEG-hRNase conjugate or PEG-hRNase analogue conjugate has a mixed degree of conjugation (e.g., a population of PEG-hRNase conjugates possessing a variety of numbers of water-soluble polymers conjugated to hRNase members of the population). In some embodiments, the PEG-hRNase conjugate or PEG-hRNase analogue conjugate is a fractionated conjugate (e.g., a population of PEG-hRNase conjugates wherein the majority of hRNase molecules (e.g., greater than 50%; greater than 60%; greater than 70%; greater than 80%; greater tha 90%; greater then 95%; greater than 97%; or more) possess the same number (e.g., one, two, three, four, five or more) of water-soluble polymers. In some embodiments, 1, 2, 3, or more polymers are conjugated to an oligomerized ribonuclease. The present invention is not limited by the number of ribonuclease molecules (e.g., hRNases) present within an oligomer. Indeed, a variety of oligomers may be conjugated to one or more water-soluble polymers including, but not limited to, oligomers of two, three, four, five, six, or even more ribonucleases (e.g., hRNases).

In some embodiments, the present invention provides a pharmaceutical composition (e.g., for treating cancer) comprising polyethylene glycol (PEG) conjugated to hRNase or a hRNase analogue, wherein at least a portion of the ribonucleolytic activity of the hRNase or hRNase analogue is retained, and a pharmaceutically acceptable carrier. In some embodiments, the conjugate comprises a degradable linkage (e.g., an ester linkage). In some embodiments, the hRNase or hRNase analogue conjugated to the polymer is less immunogenic than non-conjugated hRNase or hRNase analogue. In some embodiments, the hRNase or hRNase analogue conjugated to the polymer has a greater half-life and serum concentration than non-conjugated hRNase or hRNase analogue (e.g., due to decreased affinity between the hRNase-PEG conjugate and ribonuclease inhibitor (RI)).

In some embodiments, the present invention provides a composition comprising a plurality of conjugates, preferably although not necessarily, each having one to three water-soluble polymers covalently attached to a hRNase, wherein each water-soluble polymer preferably has a nominal average molecular weight in the range of greater than 5,000 Daltons to about 100,000 Daltons. In some embodiments, the water-soluble polymer of the conjugate is a poly(alkylene oxide). In some embodiments, the water-soluble polymers is a poly(ethylene glycol). In some embodiments, the present invention provides a composition comprising a plurality of hRNases (e.g., hRNase1) that comprise a single water-soluble polymer (e.g., that are monoPEGylated). In some embodiments, the plurality of hRNases comprise monomers, dimers, trimers, and/or higher order complexes (i.e., oligomers) of hRNases.

In some embodiments, the present invention provides a method for preparing polymer conjugates comprising the steps of contacting one or more activated, water-soluble polymers to a hRNase under conditions sufficient to result in a plurality of conjugates comprising hRNase covalently attached to the polymers. For example, in some embodiments, the present invention provides a method for preparing a water-soluble polymer-hRNase conjugate comprising the step of contacting, under conjugation conditions, a hRNase with a polymeric reagent. The present invention is not limited by the method utilized for conjugating hRNase to a water-soluble polymer. Indeed, a variety of chemistries may be used including, but not limited to, reductive amination.

Similarly, the present invention is not limited by the type of polymer used for conjugation. Indeed, a variety of polymers may be used including, but not limited to, poly(alkylene oxide), poly(vinyl pyrrolidone), poly(vinyl alcohol), polyoxazoline, poly(acryloylmorpholine), and combinations thereof. It is particularly, preferred, however, that a poly(alkylene oxide) such as a poly(ethylene glycol) derivative is used as the polymer in the present invention. In some embodiments, hRNase is contacted with an activated water-soluble polymer in order to generate a conjugate of the present invention. Activation of the water-soluble polymer can be accomplished under any art-known method so long as the resulting polymer, under the proper conditions of pH, temperature, etc., will form a covalent bond such that the hRNase covalently attaches to the polymer (e.g., contacting activated, water-soluble polymers to hRNase can be carried out under conditions sufficient for the activated, water-soluble polymer to form a covalent attachment at a desired location in the hRNase).

DESCRIPTION OF THE DRAWINGS

FIG. 1 shows amino acid residues in human pancreatic ribonucleases as well as sites modified or targeted for modification ("interest sites") located therein depicted as low interest (−), medium interest (0), or high interest (+) sites.

FIG. 10 shows the enzymatic activities of both RNase 1-aldehyde 30 kDa PEG conjugate and the RNase 1-aldehyde 40 kDa PEG conjugate.

FIG. 11 shows the efficacy of the linear 30 kDa PEG: RNase 1 conjugate relative to cisplatin and the toxicity of the agents reflected by changes in a subjects body weight in a xenograft model of cancer.

FIG. 12 shows the efficacy of the branched 40 kDa PEG: RNase 1 conjugate relative to cisplatin and the toxicity of the agents reflected by changes in a subjects body weight in a xenograft model of cancer.

FIG. 13 shows the efficacy of the branched 40 kDa PEG: RNase conjugate relative to doxorubicin in a xenograft model of cancer.

DEFINITIONS

Figure 2:
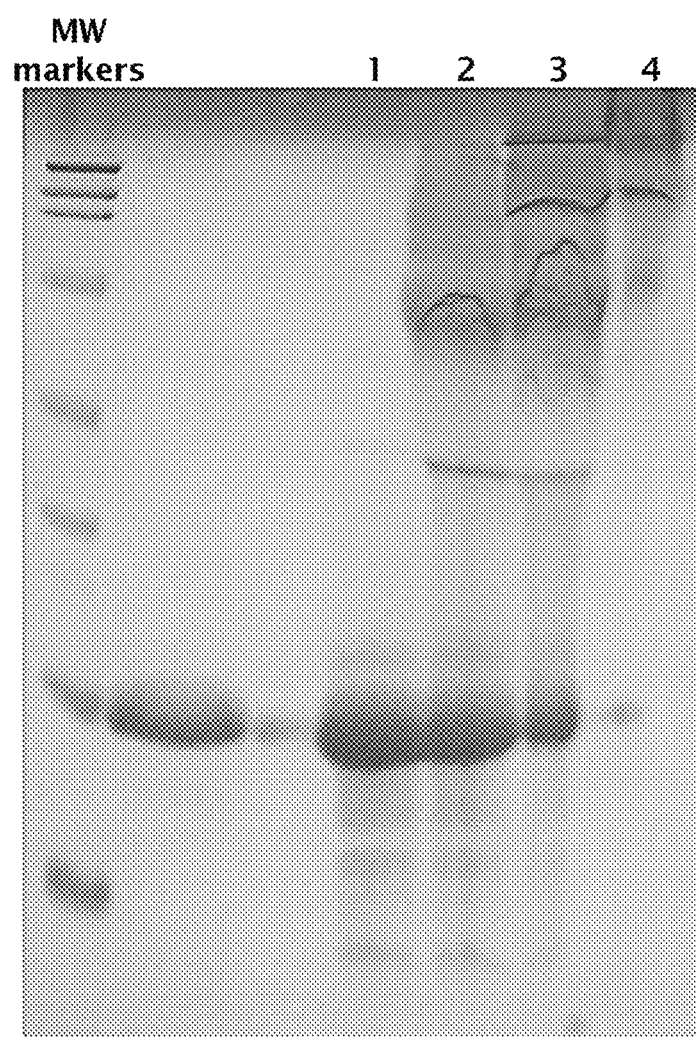
FIG. 2 shows an SDS-PAGE run on four samples of RNase A conjugated with N-hydroxy succinimide (NHS) linear 30 kDa mPEG: (1) wild type RNase A; (2) RNase:PEG (1:1) reaction; (3) RNase:PEG (1:3) reaction; and (4) RNase:PEG (1:10) reaction. A molecular weight ladder is provided for comparison (MW markers).

As used herein, the term "subject" refers to an individual (e.g., human, animal, or other organism) to be treated by the methods or compositions of the present invention. Subjects include, but are not limited to, mammals (e.g., murines, simians, equines, bovines, porcines, canines, felines, and the like), and most preferably includes humans. In the context of the invention, the term "subject" generally refers to an individual who will receive or who has received treatment for cancer As used herein, the terms "subject" and "patient" are used interchangeably, unless otherwise noted.

The term "diagnosed," as used herein, refers to the recognition of a disease (e.g., cancer) by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "effective amount" refers to the amount of a composition (e.g., a composition comprising a water-soluble polymer conjugated hRNase (e.g., PEG-conjugated hRNase1) sufficient to effect a beneficial or desired result (e.g., killing or inhibiting growth of cancer cells). An effective amount can be administered in one or more administrations, applications or dosages and is not intended to be limited to a particular formulation or administration route.

As used herein, the term "administration" refers to the act of giving a drug, prodrug (e.g., hRNase-PEG conjugate comprising a biodegradable linkage), pharmaceutical composition, or other agent, or therapeutic treatment (e.g., a composition of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), mucosal (e.g., oral mucosa or buccal), rectal, ear, by injection (e.g., intravenously, subcutaneously, intratumorally, intraperitoneally, etc.) and the like.

As used herein, the term "co-administration" refers to the administration of at least two agent(s) or therapies to a subject. In some embodiments, the co-administration of two or more agents or therapies is concurrent. In other embodiments, a first agent/therapy is administered prior to a second agent/ therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), or when a target of treatment (e.g., cancer cells) have become less sensitive (e.g., resistant) to treatment with one or more agents administered alone (e.g., that when combined with one or more other agents, such targets of treatment display increased sensitivity (e.g., are non-resistant).

As used herein, the term "toxic" refers to any detrimental or harmful effects on a subject, a cell, or a tissue as compared to the same cell or tissue prior to the administration of the toxicant.

The terms "linkage" or "linker" are used herein to refer to an atom or a collection of atoms optionally used to link interconnecting moieties such as a terminus of a polymer segment and hRNase or an electrophile or nucleophile of a hRNase. The linker of the invention may be hydrolytically stable or may include a degradable (e.g., physiologically hydrolyzable or enzymatically degradable) linkage.

As used herein, the term "degradable linkage," when used in reference to a polymer (e.g., PEG-hRNase conjugate of the present invention), refers to a conjugate that comprises a physiologically cleavable linkage (e.g., a linkage that can be hydrolyzed (e.g., in vivo) or otherwise reversed (e.g., via enzymatic cleavage). Such physiologically cleavable linkages include, but are not limited to, ester, carbonate ester, carbamate, sulfate, phosphate, acyloxyalkyl ether, acetal, and ketal linkages (See, e.g., U.S. Pat. No. 6,838,076, herein incorporated by reference in its entirety). Similarly, the conjugate may comprise a cleavable linkage present in the linkage between the polymer and hRNase, or, may comprise a cleavable linkage present in the polymer itself (e.g., such that when cleaved, a small portion of the polymer remains on the hRNase molecule) (See, e.g., U.S. Pat. App. Nos. 20050158273 and 20050181449, each of which is herein incorporated by reference in its entirety). For example, a PEG polymer comprising an ester linkage can be utilized for conjugation to hRNase to create a PEG-hRNase conjugate (See, e.g., Kuzlowski et al., Biodrugs, 15, 419-429 (2001). A conjugate that comprises a degradable linkage of the present invention is capable of generating hRNase that is free (e.g., completely or partially free) of the polymer (e.g., in vivo after hydrolysis of the linkage).

A "physiologically cleavable" or "hydrolysable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond (e.g., typically a covalent bond) that is substantially stable in water (i.e., does not undergo hydrolysis under physiological conditions to any appreciable extent over an extended period of time). Examples of hydrolytically stable linkages include, but are not limited to, carbon-carbon bonds (e.g., in aliphatic chains), ethers, amides, urethanes, and the like.

As used herein, the term "interest site" when used in reference to a ribonuclease refers to a region, subregion, and/or amino acid residue within the ribonuclease (e.g., human ribonuclease) that is modified or targeted for modification (e.g., for deletion, substitution or other type of mutation to create a ribonuclease variant, and/or for conjugation to a water-soluble polymer). Accordingly, an "interest site" may be characterized as a "high interest site," a "medium interest site," or a "low interest site" based on characteristics of the ribonuclease described herein (e.g., biologic activity (e.g., ribonucleolytic activity, cancer cell killing activity, oligomerization capacity, etc.)) desired to be retained within the ribonuclease after modification of the same (e.g., for deletion, substitution or other type of mutation to create a ribonuclease variant, and/or for conjugation to a water-soluble polymer). For example, sites that may be of interest are depicted in FIG. 1. The level of interest in modification of the residues in the ribonucleases is indicated by the use of the following symbols: low interest site ("−"), medium interest site ("0"), and high interest site ("+"). In addition, secondary structure is noted: where "a" or "a#"=alpha helix; "b" or "b#" =beta sheet. Sites of the ribonuclease that bind to substrate RNA is also labeled: "B1" and "B2"=substrate (base) binding site, "P1"=main active site, and "P2" and "P−1"=substrate (phosphate) binding sites. Cysteine residues involved in a disulfide bond are labeled by "disulf." Contact points that have been identified for the ribonuclease inhibitor are labeled with "RI". For angiogenin, the putative receptor binding site is labeled as "Rec."

As used herein, the term "pharmaceutical composition" refers to the combination of an active agent (e.g., a water-soluble polymer conjugated hRNase (e.g., PEG-conjugated hRNase1)) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions (e.g., toxic, allergic, or immunological reactions) when administered to a subject.

As used herein, the term "topically" refers to application of the compositions of the present invention to the surface of the skin and/or mucosal cells and tissues (e.g., alveolar, buccal, lingual, masticatory, vaginal, or nasal mucosa, and other tissues and cells that line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintrigrants (e.g., potato starch or sodium starch glycolate), and the like. The compositions also may include stabilizers and preservatives. Examples of carriers, stabilizers, and adjuvants are described in the art (See e.g., Martin, Remington's Pharmaceutical Sciences, 15th Ed., Mack Publ. Co., Easton, Pa. (1975), incorporated herein by reference).

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "kit" refers to any delivery system for delivering materials. In the context of reaction materials (e.g., compositions comprising a water-soluble polymer conjugated hRNase (e.g., PEG-conjugated hRNase1)), such delivery systems include systems that allow for the storage, transport, or delivery of reaction reagents and/or supporting materials (e.g., written instructions for using the materials, etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising a water-soluble polymer conjugated hRNase (e.g., PEG-conjugated hRNase1) for a particular use, while a second container contains a second agent (e.g., a second chemotherapeutic agent). Indeed, any delivery system comprising two or more separate containers that each contains a subportion of the total kit components are included in the term "fragmented kit." In contrast, a "combined kit" refers to a delivery system containing all of the components of a reaction materials needed for a particular use in a single container (e.g., in a single box housing each of the desired components). The term "kit" includes both fragmented and combined kits.

DETAILED DESCRIPTION OF THE INVENTION

In mammalian cells, pancreatic-type ribonucleases, such as bovine RNase A and human ribonuclease 1 (hRNase1), are secretory enzymes that catalyze the degradation of RNA into ribonucleotides. Their activity is inhibited by binding to ribonuclease inhibitor (RI), a ubiquitous cytosolic protein. RI binds with high affinity to endogenous pancreatic-type RNases, neutralizing their activity, thereby making them non-toxic to cells (e.g., normal or cancer cells). When RNase activity is inhibited, the cellular RNA is undamaged and the cell remains viable. In normal cells the ribonuclease activity is tightly controlled, but if ribonuclease activity is uncontrolled, the ribonucleolytic activity destroys cellular RNA leading to the death or killing of the cell.

Several approaches have been used to make ribonucleases toxic to human cells, especially cancer cells. The first approach selected for ribonucleases that are evolutionarily distant to humans and not inhibited by human RI protein. For example, the frog (*Rana pipiens*) ribonuclease, when placed in a human cell, does not display significant inhibition by human RI, thereby remaining active (e.g., degrading RNA) leading to the death of the cell.

The second approach utilizes recombinant DNA technology to make mammalian ribonuclease mutants that display high levels of ribonucleolytic activity (e.g., because they are not significantly inhibited by human RI). These mutated enzymes provide high levels of ribonucleolytic activity within cancer cells because they evade association with and binding to RI or because they possess other biological activity (e.g., the ability to kill cancer cells). This unregulated activity can be particularly lethal to cancer cells. This mutation approach has been demonstrated with the mammalian proteins bovine RNase A and human RNase I and is described in U.S. Pat. Nos. 5,389,537 and 6,280,991, the disclosures of which are herein incorporated by reference in their entireties.

The mammalian (e.g., human) pancreatic ribonucleases are small proteins with molecular weights around 14 kDa. These proteins are cleared very quickly via the kidneys. Thus, improving the pharmacokinetic profile of the ribonucleases without significantly impacting the features that endow their efficacy (e.g., their ribonucleolytic activity) and safety profiles is desirable. To this end, although an understanding of the mechanism is not necessary to practice the present invention and the present invention is not limited to any particular mechanism of action, conjugation of human ribonucleases to a water-soluble polymer, in some embodiments, improves the efficacy and pharmacokinetics of the of the ribonucleases (e.g., internalization, sustained enzymatic activity, capacity for cellular degradation, etc.) due to evasion of the ribonucleases from RI, by stabilizing the enzymatic activity of the proteins, or by other mechanisms.

The present invention provides methods of modifying ribonucleases (e.g., human ribonucleases (e.g., hRNase1)) without the loss of enzymatic activity or loss of other desired properties of these proteins (e.g., cancer cell killing capacity and/or oligomerization capacity), and compositions comprising such modified ribonucleases (See, e.g., Examples 1-7). Thus, in some embodiments, the present invention provides a modified ribonuclease (e.g., hRNase or hRNase analogue conjugated to a water-soluble polymer) that is more toxic to cells (e.g., cancer cells) in vivo compared to non-modified hRNase. In some embodiments, the modified ribonuclease is more toxic to cancerous cells compared to non-cancerous cells and is targetable to a specific tumor. In some embodiments, the modified ribonuclease has few side effects and does not stimulate a human immune response, or stimulates less of an immune response than does a non-modified hRNase (See, e.g., Examples 6 and 7). Thus, the present invention provides modified ribonucleases (e.g., hRNases (e.g., water-soluble polymer conjugates)) that are derived from wild-type or mutated ribonucleases that exhibit low immunogenicity and side effects while maintaining detectable amounts (e.g., greater than 1 %, greater than 5%; greater than 10%; greater than 20%; greater than 30%; greater than 40%; greater than 50%; greater than 60%; greater than 70%; greater than 80%; greater than 90%; greater than 95%; greater than 97%) of ribonucleolytic activity (e.g., thereby resulting in cellular- (e.g., cancer cell-) specific toxicity or tumor growth inhibition activity (See, e.g., Examples 6 and 7).

The terms "human ribonuclease," "hRNase" and functional equivalents include wild type human ribonucleases (e.g., human pancreatic ribonucleases (e.g., hRNase1, hRNase2, hRNase3, hRNase4, hRNase5, hRNase6, hRNase7, hRNase8)) and any hRNase mutant or variant, any recombinant, or related enzyme, or any synthetic version or fragment of hRNases that retain the ribonucleolytic activity or other desired properties (e.g., cancer cell killing, capable of degrading RNA), in vivo and in vitro. Variants may be generated by post-translational processing of the protein (e.g., by enzymes present in a producer strain or by means of enzymes or reagents introduced at any stage of a manufacturing process) or by mutation of the structural gene. Mutations may include site deletion, insertion, domain removal and replacement mutations.

The term "hRNase analogue" is defined as including any form of hRNases that are not wild-type. The hRNase and hRNase analogues contemplated in the present invention may be recombinantly expressed (e.g., from a cell culture or higher recombinant species such as a mouse or otherwise, expressed in mammalian cell hosts, insects, bacteria, yeast, reptiles, fungi, etc.), or synthetically constructed. This includes the activity retaining synthetic construction including synthetic peptides and polypeptides or recombinant expression of portions of the hRNase polypeptide responsible for its enzymatic activity, or as part of a larger protein or polypeptide, including chimeric proteins.

Thus, recombinant or synthetically produced hRNase preparations can be used that contain only the active form of hRNases. The recombinant expression of homogenous hRNase, and homogenous fully active hRNase (e.g., containing compositions prepared from the expressed wild-type protein or analogues thereof) have been described (See, e.g., U.S. Pat. App. Pub. No. 20050261232, published Nov. 24, 2005, the disclosure of which is incorporated herein by reference in its entirety).

In some embodiments, the present invention utilizes hRNase analogues to prevent, treat or cure diseases, particularly cancer and viral infections. The compositions also find use in diagnostic applications (e.g., associated with drug screening or cancer characterization) and research applications. In some embodiments, the hRNases are engineered (e.g., through recombinant DNA techniques (e.g., genetic engineering of hRNase analogues)) to be toxic to the cells to which they are delivered. Thus, in some embodiments, the hRNase itself (e.g., in addition to covalent conjugation with a water-soluble polymer) is engineered to be less susceptible to naturally occurring inhibitors of the hRNase and/or to evade the host immune system.

The present invention is not limited by the type of ribonuclease utilized for modification by the methods described herein. In some embodiments, the ribonuclease is a bovine ribonuclease. In some embodiments, the ribonuclease is a frog ribonuclease. In some embodiments, the ribonuclease is a human ribonuclease. In some embodiments, the ribonuclease is eosinophil-derived neurotoxin (EDN/RNase 2) (See, e.g., Domachowske et al., Nucleic Acids Res 26(23): 5327-32 (1998)). In some embodiments, the ribonuclease is angiogenin. In some embodiments, the ribonuclease is human eosinophil cationic protein (ECP) (See, e.g., Sorrentino and Glitz, FEBS Lett. 288(1-2):23-6 (1991).

In some embodiments, the present invention provides polymer conjugation of bovine ribonucleases (e.g., ribonuclease A) to increase its circulating half-life in vivo while retaining ribonuleolytic activity or other desired function (e.g., cancer cell killing). In some embodiments, ribonuclease A is conjugated to a water-soluble polymer in a region of the protein involved in evasion from ribonuclease inhibitor (RI). In some preferred embodiments, ribonuclease A is conjugated to a water-soluble polymer in a region of the protein that is not involved in evasion from RI (e.g., a region that has no impact on binding of ribonuclease A to the RI). Examples of regions that are not involved in evasion from RI include, but are not limited to, regions comprising amino acid residues at positions 1, 49, 75 or 113. Thus, although an understanding of the mechanism is not necessary to practice the present invention and the present invention is not limited to any particular mechanism of action, in some embodiments, conjugation of a water soluble polymer to ribonuclease A possess biological activity (e.g., cancer cell killing) even though the conjugation does not assist the ribonuclease from evading the RI.

In some embodiments, the ribonuclease is a human ribonuclease. In some embodiments, the present invention utilizes incorporation of a unique functional group in hRNases for conjugation of a water-soluble polymer. For example, in some embodiments, a cysteine molecule is engineered into a hRNase (e.g., without loss of ribonucleolytic acitivity or other desired function (e.g., cancer cell killing capacity)) in order to provide a free thiol group for conjugation to a water-soluble polymer. Free thiol groups are not found elsewhere in the RNase thereby providing the ability to generate a homogenous conjugation. In other embodiments, recombinant DNA technology is utilized to provide modified or novel codons to incorporate non-natural amino acids with orthogonal functionality into the hRNase of interest (e.g., without loss of ribonucleolytic activity).

In preferred embodiments, the desired residues for modification (e.g., deletion, mutation, and/or conjugation to a water-soluble polymer) in human ribonucleases (e.g., hRNase 1) are selected to avoid disruption of the tertiary structure and/or stability of the ribonuclease. In some embodiments, these residues are on the surface of the protein (e.g., residues generally exposed to solvent (e.g., water or buffer). For example, in some embodiments, the types of residues that are modified include, but are not limited to, amino acids that appear disordered in crystal structures, residues that contact the ribonuclease inhibitor protein, and amino acids not involved in tertiary structures (e.g., alpha helices and beta sheets), amino acids in loop regions between structures (e.g. alpha helices and beta sheets) as well as amino acids towards the end of the protein (the N— and C-termini). In some embodiments, additional amino acid residues are added to either the N— or C-terminus (e.g., to generate a RNase analogue and/or for conjugation of a water-soluble polymer).

In some embodiments, ribonucleases are modified to include one or more amino acid residues such as, for example, lysine, cysteine and/or arginine, in order to provide an attachment location for water-soluble polymer (e.g., to an atom within the side chain of the amino acid). Techniques for adding amino acid residues are well known to those of ordinary skill in the art (See, e.g., March, Advanced Organic Chemistry: Reactions Mechanisms and Structure, 4th Ed. (New York: Wiley-Interscience, 1992).

The present invention is not limited by the type of modification made to a ribonuclease (e.g, hRNase) described herein. In some embodiments, a ribonuclease (e.g., hRNase) of the present invention is modified through the attachment of one or more moieties selected from the group comprising dextran, carbohydrate, albumin, carrier protein, and antibody (e.g., a non-targeting antibody used to extend the half-life of the ribonuclease).

In some embodiments, an amino acid in a tertiary structure is modified whose side chains are accessible to a solvent (e.g., buffer or water) without disturbing the tertiary structure. For example, not all changes within tertiary structures are negative as evidenced by literature reports that describe cysteine residues that form disulfides where the cysteine is located within a beta sheet (e.g., Cys 84).

In some embodiments, amino acids within hRNases that, if modified, destroy or significantly inhibit enzymatic activity and/or substrate binding are not targeted for modification. In some embodiments, amino acids within hRNases that, if modified, destroy or significantly inhibit enzymatic activity and/or substrate binding are specifically targeted for modification.

Amino acid residues for human pancreatic ribonucleases are provided in FIG. 1. The present invention provides a ranking of the utility for modification of each amino acid (e.g., as represented by interest in modifying (e.g., so as to result in a functional ribonuclease (e.g., comprising a desired property (e.g., cancer cell killing and/or ribonucleolytic activity)))). The amino acids are labeled in FIG. 1 as follows:

low interest (−),
medium interest (0), or
high interest (+).

It will be appreciated that one or more modification sites may be used. Preferably, the selected sites are high interest sites. However, one or more medium interest or low interest sites may be used as desired and appropriate for the intended application. It should be noted that, in some embodiments, human RNase is produced (e.g., in vitro, in vivo or ex vivo) in such a way that a methionine (e.g., that is not part of wild type human RNase) is incorporated as the first amino acid of the protein (e.g., via the methods used to produce the protein (e.g., recombinant human ribonuclease (e.g., produced in *E. coli*))). Thus, in some embodiments, the numbering of amino acid residues depicted in FIG. 1 may be off by a numerical value of one (e.g., if a methionine is incorporated into the protein, than the numbering of the amino acid residues of the human RNases shown in FIG. 1 is off by 1 (i.e., because a methionine is incorporated in position 1, the numbering of the amino acids depicted in FIG. 1 will be short by one, e.g., the residue number 10 would actually be residue number 11 because of the methionine incorporated at position 1)). Similarly, the positions depicted in FIG. 1 may also be applied to corresponding numerical positions in RNase A (e.g., bovine).

In some embodiments, the present invention utilizes digestion of hRNases to produce S-peptide and S-protein to produce protein that is conjugated to a water-soluble polymer (See, e.g., Hamachi et al., Bioorg Med Chem Lett 9, 1215-1218 (1999); Goldberg and Baldwin, Proc Natl Acad Sci, 96, 2019-2024 (1999); Asai et al., J Immun Meth, 299, 63-76 (2005); Backer et al., J Cont Release, 89, 499-511 (2003); Backer et al., Bioconj Chem, 15, 1021-1029 (2004)). For example, digestion of bovine RNase A by subtilisin results primarily in two fragments due to cleavage between Ala20 and Ser21. The shorter fragment (amino acids 1-20) is referred to as S-peptide, whereas the longer fragment (amino acids 20-124) is referred to as S-protein. The two fragments bind tightly at neutral pH and are sometime referred to as RNase S or RNase S'. RNase S is an active ribonuclease. The S-peptide-S-protein interaction has been used for affinity purification as well as in tertiary docking systems to target imaging agents or drugs. Thus, in some embodiments, the present invention provides creation of a similar S-peptide-S-protein for human ribonucleases.

In some embodiments, conjugation of the S-peptide component to a water-soluble polymer is contemplated to allow activity of the ribonuclease to be maintained within the RNase S enzyme upon combination with S-protein. For example, while there are lysine residues within the first 20 amino acids of hRNase 1 (at positions 1, 6, and 7), none of these residues appear critical for enzymatic activity at the lysine 41 position. Thus, in some embodiments, conjugation to a water soluble polymer of lysine molecules within the S-peptide takes place prior to association with the S-protein, thereby leaving lysine at position 41 non-modified (e.g., conjugated to water soluble protein), thereby providing a RNase S enzyme conjugated to water soluble polymer that retains enzymatic activity. In some embodiments, the S-protein component is used for conjugation and then added to the S-peptide portion to attain RNase S enzyme function.

The present invention is not limited by the type of water-soluble polymer utilized for conjugation to a human ribonuclease described herein. Indeed, any biocompatible water-soluble polymer may be used. In some embodiments, the water-soluble polymer is nonpeptidic, nontoxic, non-naturally occurring and/or biocompatible. A water-soluble polymer is considered biocompatible if the beneficial effects associated with use of the polymer alone or with another substance (e.g., conjugated to a hRNase (e.g., hRNase1)) in connection with living tissues (e.g., administration to a patient) outweighs any deleterious effects as evaluated by a clinician (e.g., a physician). With respect to non-immunogenicity, a polymer is considered nonimmunogenic if the intended use of the polymer in vivo does not produce an undesired immune response (e.g., the formation of antibodies) or, if an immune response is produced, that such a response is not deemed clinically significant or important as evaluated by a clinician. Thus, in some preferred embodiments, the water-soluble polymer is biocompatible and non-immunogenic.

Water-soluble polymers of the present invention are selected such that, when attached to a human ribonuclease, the polymer does not precipitate in an aqueous environment, such as a physiological environment. In some embodiments, the polymer is selected based upon the method of conjugation to the human ribonuclease protein. For example, for methods utililizing reductive alkylation, the polymer selected should have a single reactive aldehyde so that the degree of polymerization may be controlled. The polymer may be branched or unbranched. Preferably, for therapeutic use of the end-product preparation, the polymer will be pharmaceutically acceptable. One skilled in the art will be able to select the desired polymer based on such considerations as whether the polymer/protein conjugate will be used therapeutically, and if so, the desired dosage, circulation time, resistance to proteolysis, and other considerations. For example, these may be ascertained by assaying for ribonucleolytic activity of the conjugate in vitro using methods well known in the art.

The water-soluble polymer may be selected from the group including, but not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(.alpha.-hydroxy acid), poly(vinyl alcohol), polyphosphazene, polyoxazoline, poly(N-acryloylmorpholine), and combinations of any of the foregoing.

The polymer may be linear (e.g., alkoxy PEG or bifunctional PEG) or branched. Furthermore, the polymer may be multi-armed (e.g., forked PEG or PEG attached to a polyol core), dendritic, and/or comprise degradable linkages. It is contemplated that the internal structure of the polymer can be organized in any of a number of different patterns (e.g., patterns including, but not limited to, homopolymer, alternating copolymer, random copolymer, block copolymer, alternating tripolymer, random tripolymer, and block tripolymer).

Furthermore, the polymer may be "activated" with a suitable activating group appropriate for coupling to a desired residue within a ribonuclease (e.g., hRNase). An "activated" polymer refers to a polymer that possesses reactive groups for reaction with a ribonuclease (e.g., hRNase1). Examples of activated polymers and methods for their conjugation to proteins that are contemplated to be useful (e.g., for conjugating a water-soluble polymer to a human ribonuclease) in the present invention are known in the art and are described in detail in Zalipsky, Bioconjugate Chem 6, 150-165 (1995); Kinstler et al., Advanced Drug Delivery Reviews 54, 477-485 (2002); and Roberts et al., Advanced Drug Delivery Reviews 54, 459-476 (2002); each of which is hereby incorporated by reference in its entirety for all purposes.

The polymer may be of any molecular weight. For example, for polyethylene glycol, a preferred molecular weight is between about 2 kDa and about 150 kDa (the term "about" indicating that in preparations of polyethylene glycol, some molecules will weigh more, some less, than the stated molecular weight). Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic composition of the present invention (e.g., comprising a hRNase protein or analog)).

When polyethylene glycol (PEG) is utilized as the water soluble polymer, PEG may have one of its termini capped with an inert group. For example, the PEG molecule may be methoxy-PEG, also referred to as mPEG, which is a form of PEG wherein one terminus of the polymer is a methoxy (i.e., —OCH$_3$) group, while the other terminus is a functional group (e.g., hydroxyl) that can be chemically modified and used for conjugation to a reactive group on a target protein (e.g., human ribonuclease). In some embodiments, a PEG polymer described in U.S. Pat. App. Pub. No. 20040235734 is used.

In some embodiments, the PEG polymer may comprise one or more weak or degradable linkages. For example, a PEG polymer may comprise an ester linkage (e.g., that may hydrolyze over time (e.g., when present within a patient)). In some embodiments, hydrolysis of the PEG polymer comprising a degradable linkage produces two or more fragments (e.g., of lower molecular weight than the parent molecule).

The present invention is not limited by the type of degradable linkage. Indeed, a PEG polymer may comprise one or more of a variety of degradable linkages including, but not limited to, carbonate linkages; imine linkages; phosphate ester linkages; hydrazone linkages; acetal linkages; orthoester linkages; amide linkages, urethane linkages; peptide linkages; and oligonucleotide linkages.

It is contemplated that the inclusion of one or more degradable linkages within the polymer itself provides an added mechanism to control the pharmacokinetic characteristics of the conjugates of the present invention. For example, in some embodiments, a hRNase-PEG conjugate of the present invention may be administered to a patient wherein the conjugate, when administered, possesses little to no enzymatic activity, but when exposed to conditions such that the linkages degrade (e.g., hydrolyze), the ribonucleolytic activity of the enzyme is activated. Thus, in some embodiments, the degradable linkages within the PEG molecule can be used for increasing specificity and efficacy of the conjugate.

It is contemplated that the conjugates of the present invention may comprise a linkage between the polymer (e.g., PEG) and human ribonuclease protein. In some embodiments, the linkage is a stable linkage (e.g., amide linkage, carbamate linkage, amine linkage, thioether/sulfide linkage, or carbamide linkage. In some embodiments, the linkage is hydrolytically degradable (e.g. to allow release of the hRNase (e.g., without a portion of the polymer (e.g., PEG) remaining on the hRNase)). The present invention is not limited by the type of degradable linkage utilized. Indeed, a variety of linkages are contemplated herein including, but not limited to, carboxylate ester, phosphate ester, thiolester, anhydrides, acetals, ketals, acyloxyalkyl ether, imines, orthoesters, peptides and oligonucleotides. These linkages may be prepared by modification of either the hRNase protein (e.g., at the C-terminal carboxyl group, or a hydroxyl group of an amino acid side chain) and/or the polymer (e.g., using methods known in the art).

The proportion of water-soluble polymer (e.g., PEG) to ribonuclease (e.g., hRNase) protein molecules may vary, as may their concentrations in the reaction mixture. In general, the optimum ratio (e.g., in terms of efficiency of reaction (e.g., to conjugate polymer to one, two three, four or more sites) where there is little to no excess unreacted protein or polymer) can be determined (e.g., using the molecular weight of the polymer (e.g., PEG) selected, conjugation chemistry utilized, number of interest sites targeted, etc.). For example, in some embodiments, a non-specific conjugation reaction (e.g., PEGylation reaction) can be carried out followed by a later purification (e.g., to separate hRNases based upon the number of polymers (e.g., PEGs) conjugated to each hRNase).

In some embodiments, the conjugates are present within a composition. For example, in some embodiments, the composition comprises a plurality of conjugates, wherein each protein comprises 1-3 water-soluble polymers covalently attached to the protein. In some embodiments, the composition comprises a plurality of conjugates, wherein each protein comprise 1, 2, 3, 4, 5, 6, or more polymers attached to the protein. In some embodiments, the composition comprises a population of conjugates wherein the majority of conjugates (e.g., greater than 65%, greater than 70%, greater than 75%, greater than 80%, greater than 85%, greater than 90%, greater than 95%, greater than 97%, greater than 98%, greater than 99%) are covalently attached to the same number (e.g., 1, 2, 3, or more) of polymers (e.g., PEG molecules). In some embodiments, 1, 2, 3, or more polymers are conjugated to an oligomerized ribonuclease. The present invention is not limited by the number of ribonuclease molecules (e.g., hRNases) present within an oligomer. Indeed, a variety of oligomers may be conjugated to one or more water-soluble polymers including, but not limited to, oligomers of two, three, four, five, six, or even more ribonucleases (e.g., hRNases). In some embodiments, the present invention provides a composition comprising a plurality of hRNases (e.g., hRNase1) that comprise a single water-soluble polymer (e.g., that are monoPEGylated). In some embodiments, the plurality of hRNases comprise monomers, dimers, trimers, and/or higher order complexes (i.e., oligomers) of hRNases.

In preferred embodiments, the modified human ribonuclease proteins (e.g., water-soluble polymer-hRNase conjugates) of the present invention retain a significant portion of enzymatic (e.g., ribonucleolytic) activity. In some embodiments, the conjugate possesses from about 1% to about 95% of the enzymatic activity of the unmodified (e.g., non-conjugated) ribonulcease. In some embodiments, the conjugate possesses more activity than the unmodified ribonuclease. In some embodiments, a modified human ribonuclease possesses about 1%, 5%, 10%, 15%, 20%, 30%, 40%, 50%, 55%, 60%, 65%, 70%, 75%, 80%, 85%, 90%, 95%, 97%, 99%, 100%, or more relative to that of the unmodified parent ribonulcease possessing ribonucleolytic activity (e.g., as measured in an in vitro assay well known to those of skill in the art).

In other preferred embodiments, the modified human ribonuclease proteins (e.g., water-soluble polymer-hRNase conjugates) of the present invention retain a significant portion of another desired property (e.g., other than ribonucleolytic activity (e.g., cancer cell killing capacity)). Although an understanding of the mechanism is not necessary to practice the present invention and the present invention is not limited to any particular mechanism of action, in some embodiments, a modified human ribonuclease protein (e.g., water-soluble polymer-hRNase conjugate) is capable of killing target cells (e.g., cancer cells or microbially (e.g., virally) infected cells) in the absence of (e.g., less than 70%, less than 60%, less than 50%, less than 40%, less than 30%, less than 20%, less than 10%, or less than 5% of unmodified ribonuclease) ribonucleolytic activity (e.g., due to other characteristics of the human ribonuclease protein).

The present invention is not limited by the method utilized for conjugating a water-soluble polymer to a human ribonuclease of the present invention. Multiple types of chemistries are known in the art and may find use in the generation of the compositions of the present invention. These methods have been describe in detail (See, e.g., Zalipsky, Bioconjugate Chem 6, 150-165 (1995); Kinstler et al., Advanced Drug Delivery Reviews 54, 477-485 (2002); and Roberts et al., Advanced Drug Delivery Reviews 54, 459-476 (2002)). In some embodiments, the present invention utilizes a conjugation chemistry useful for conjugating an activated polymer of the present invention to a human ribonuclease.

For example, for obtaining N-terminally conjugated hRNase (e.g., N-terminally PEGylated hRNase), reductive alkylation may be used. A method for attaching without a linking group between the polymer (e.g., PEG) and the protein moiety is described in Francis et al., In: Stability of protein pharmaceuticals: in vivo pathways of degradation and strategies for protein stabilization (Eds. Ahem., T. and Manning, M. C.) Plenum, N.Y., 1991). In some embodiments, a method involving the use of N-hydroxy succinimidyl esters of carboxymethyl mPEG is used (See, e.g., U.S. Pat. No. 5,824,784, issued Oct. 20, 1998, hereby incorporated by reference in its entirety).

In some embodiments, the PEG-ribonuclease conjugate is purified after conjugation. The present invention is not limited by the type of purification process utilized. Indeed, a variety of processes may be utilized including, but not limited to, gel filtration chromatography, ion exchange chromatography, hydrophobic interaction chromatography, size exclusion chromatography, and other methods well known in the art.

For example, in some embodiments, a water-soluble polymer-hRNase conjugate can be purified to obtain one or more different types of conjugates (e.g., a conjugate covalently bound to a single polymer). In some embodiments, the products of a conjugation reaction are purified to obtain (e.g., on average) anywhere from 1, 2, 3, 4, or more polymers (e.g., PEGs) per human ribonuclease. In some embodiments, gel filtration chromatography is used to separate/fractionate ribonucleases covalently attached to different numbers of polymers or to separate a conjugate from non-conjugated protein or from non-conjugated polymer. Gel filtration columns are well known in the art and available from multiple sources (e.g., SUPERDEX and SEPHADEX columns from Amersham Biosciences, Piscataway, N.J.).

In some embodiments, the present invention provides a composition comprising a water-soluble polymer-human ribonuclease conjugate. In some embodiments, the composition is administered to a patient in order to treat cancer. Thus, in some embodiments, the present invention provides a method of treating cancer comprising administering a composition comprising a water-soluble polymer-human ribonuclease conjugate.

The dose of a composition comprising a water-soluble polymer-human ribonuclease conjugate may vary depending upon th age, weight, and general condition of the subject as well as the severity of the condition (e.g., cancer) to be treated and the type of polymer-ribonuclease conjugate administered. Effective amounts (e.g., therapeutically effective amounts) are known to those skilled in the art. In general, a therapeutically effective amount will range from about 0.001 mg to about 500 mg (e.g., from 0.01 mg to 100 mg) per day administered to a patient in one or more doses, although the present invention is not limited by the dose utilized (e.g., less than 0.001 mg or more the 500 mg may be administered to a patient in one or more doses). Alternatively, a dose may be given one or more times a week, or one or more times a month, or a combination of any of the preceding doses.

In some embodiments, the conjugate is co-administered with one or more other agents. It is contemplated that, in some embodiments, when a composition comprising a water-soluble polymer-human ribonuclease conjugate is co-administered with another agent (e.g., an anti-cancer agent), a smaller dose of one or both of the agents may be administered to a patient without loss of therapeutic benefit (e.g., thereby decreasing unwanted side effects or reducing the potential for drug resistance). The present invention is not limited to the treatment of cancer. Indeed, a composition of the present invention may be administered to a subject to treat any condition or disease that may benefit (e.g., that can be remedied or prevented) using the compositions and methods of the present invention. The invention provides therapeutic modalities and pharmaceutical compositions for the treatment of cancer, tumorigenesis and the prevention of transformed phenotypes.

In some embodiments, the present invention provides therapies for cancer. In some embodiments, therapies provide a water-soluble polymer-human ribonuclease conjugate for the treatment of cancers.

In some embodiments, a water-soluble polymer-human ribonuclease conjugate can be administered systemically or locally to kill tumor cells, inhibit tumor cell proliferation and angiogenesis, and/or induce tumor cell death in cancer patients. They can be administered intravenously, intrathecally, intraperitoneally as well as orally. Moreover, they can be administered alone or in combination with anti-proliferative drugs or other anti-cancer agents.

Where combinations are contemplated, it is not intended that the present invention be limited by the particular nature of the combination. The present invention contemplates combinations as simple mixtures as well as chemical hybrids.

It is not intended that the present invention be limited by the particular nature of the therapeutic preparation. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations for cancer usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. Specific excipients, antimicrobials, antioxidants, and surfactants that find use in a pharmaceutical composition comprising a water-soluble polymer are described in U.S. Pat. App. Pub. No. 20040235734, hereby incorporated by reference in its entirety.

The compositions can also be prepared as injectables, either as liquid solutions or suspensions; solid forms suitable for solution in, or suspension in, liquid prior to injection may also be prepared.

The compositions of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

The methods of the present invention can be practiced in vitro or in vivo.

For example, the method of the present invention can be used in vitro to screen for compounds which are useful for combinatorial use with a water-soluble polymer-human ribonuclease conjugate for treating cancer (e.g., prostate, lung, stomach, breast, colon, and/or pancreatic cancer); to evaluate a compound's efficacy in treating cancer; or to investigate the mechanism by which a compound combats cancer (e.g., whether it does so by inducing apoptosis, by inducing differentiation, by decreasing proliferation, etc). For example, once a compound has been identified as a compound that works in combination with a water-soluble polymer-human ribonuclease conjugate to inhibit angiogenesis, proliferation and/or killing (e.g., cause apoptosis) of cancer cells, one skilled in the art can apply the method of the present invention in vitro to evaluate the degree to which the compound induces killing/apoptosis and/or decreases angiogenesis, proliferation of cancer cells; or one skilled in the art can apply the method of the present invention to determine whether the compound operates by inducing apoptosis, by decreasing proliferation and/or angiogenesis, or by a combination of these methods.

Alternatively, the method of the present invention can be used in vivo to treat cancers, (e.g., including, but not limited to, prostate cancer, lung cancer, stomach cancer, pancreatic cancer, breast cancer, and colon cancer). In the case where the method of the present invention is carried out in vivo, for example, where the cancer cells are present in a human subject, contacting can be carried out by administering a therapeutically effective amount of the compound to the human subject (e.g., by directly injecting the therapeutic (e.g., comprising a water-soluble polymer-human ribonuclease conjugate) into a tumor or through systemic administration).

The present invention, in another aspect thereof, relates to a method of treating cancer, such as prostate cancer, lung cancer, stomach cancer, breast cancer, pancreatic cancer, colon cancer, or other cancers. The method includes administering to the subject an amount of a compound effective to inhibit angiogenesis, proliferation and/or cause the death of cancer cells.

The present invention is not limited by the type of cancer treated. Indeed, a variety of cancers can be treated using a composition comprising a water-soluble polymer-human ribonuclease conjugate of the present invention including, but not limited to, acute lymphocytic leukemia, acute myelocytic leukemia, acoustic neuroma, adenocarcinoma, angiosarcoma, astrocytoma, basal cell carcinoma, bile duct carcinoma, bladder carcinoma, bone originated tumor, bone sarcoma, brain tumor, breast cancer, bronchogenic carcinoma, carcinoma, cervical cancer, chondrosarcoma, chordoma, choriocarcinoma, chronic lymphocytic leukemia, colon carcinoma, craniopharyngioma, cystadenocarcinoma, embryonal carcinoma, endotheliosarcoma, ependymoma, epithelial carcinoma, esophageal carcinoma, Ewing's tumor, fibrosarcoma, glioma, heavy chain disease, hemangioblastoma, hepatic carcinoma, hodgkin's lymphoma, leiomyosarcoma, leukemia, liposarcoma, lung carcinoma, lymphangioendotheliosarcoma, lymphangiosarcoma, medullary carcinoma, medulloblastoma, melanoma, meningioma, mesothelioma, multiple myeloma, myxosarcoma, neuroblastoma, non-Hodgkin's lymphoma, pancreatic cancer, oligodendroglioma, osteogenic sarcoma, ovarian cancer, pancreatic carcinoma, papillary carcinoma, papillary adenocarcinoma, pinealoma, polycythemia vera, acute promyelocytic leukemia, prostate cancer, rectal cancer, renal cell carcinoma, retinoblastoma, rhabdomyosarcoma, sarcoma, sebaceous gland carcinoma, seminoma, small cell lung carcinoma, squamous cell carcinoma, stomach carcinoma, synovioma, sweat gland carcinoma, testicular tumor, uterus carcinoma, Waldenstrom's macroglobulinemia, and Wilms' tumor.

Suitable subjects that may be administered a composition comprising a water-soluble polymer-human ribonuclease conjugate include, for example mammals, such as rats, mice, cats, dogs, monkeys, and humans. Suitable human subjects include, for example, those which have previously been determined to be at risk of having cancer (e.g., prostate cancer, lung cancer, stomach cancer, pancreatic cancer, colon cancer, and, breast cancer) and those who have been diagnosed as having cancer.

In subjects who are determined to be at risk of having cancer, the compositions of the present invention are administered to the subject preferably under conditions effective to decrease angiogenesis, proliferation and/or induce killing (e.g., apoptosis) of cancer cells in the event that they develop.

The compositions herein may be made up in any suitable form appropriate for the desired use. Examples of suitable dosage forms include oral, parenteral, or topical dosage forms.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

In addition to a water-soluble polymer-human ribonuclease conjugate, pharmaceutical compositions can include other active materials, particularly, actives which have been identified as useful in the treatment of cancers. These actives can be broad-based anti-cancer agents, such that they also are useful in treating more than one type of cancer or they may be more specific (e.g., in a case where the other active material is useful for treating a specific type of cancer (e.g., adenocarcinoma) but not useful for treating a second type of cancer (e.g., oral squamous cell carcinoma). The other actives can also have non-anti-cancer pharmacological properties in addition to their anti-cancer properties. For example, the other actives can have anti-inflammatory properties, or, alternatively, they can have no such anti-inflammatory properties.

It will be appreciated that the actual preferred amount of composition comprising a water-soluble polymer-human ribonuclease conjugate to be administered according to the present invention may vary according to the particular composition formulated, and the mode of administration. Many factors that may modify the action of the compositions (e.g., body weight, sex, diet, time of administration, route of administration, rate of excretion, condition of the subject, drug combinations, and reaction sensitivities and severities) can be taken into account by those skilled in the art. Administration can be carried out continuously or periodically within the maximum tolerated dose. Optimal administration rates for a given set of conditions can be ascertained by those skilled in the art using conventional dosage administration tests.

A wide range of therapeutic agents find use with the present invention. For example, any therapeutic agent that can be co-administered with a water-soluble polymer-human ribonuclease conjugate is suitable for use in the present invention.

Some embodiments of the present invention provide administering to a subject an effective amount of a water-soluble polymer-human ribonuclease conjugate (and enantiomers, derivatives, and pharmaceutically acceptable salts thereof) and at least one anticancer agent (e.g., a conventional anticancer agent, such as, chemotherapeutic drugs, and/or radiation therapy).

Anticancer agents suitable for use with the present invention include, but are not limited to, agents that induce apoptosis, agents that induce/cause nucleic acid damage, agents that inhibit nucleic acid synthesis, agents that affect microtubule formation, and agents that affect protein synthesis or stability.

Classes of anticancer agents suitable for use in compositions and methods of the present invention include, but are not limited to: 1) alkaloids, including, microtubule inhibitors (e.g., Vincristine, Vinblastine, and Vindesine, etc.), microtubule stabilizers (e.g., Paclitaxel (Taxol), and Docetaxel, etc.), and chromatin function inhibitors, including, topoisomerase inhibitors, such as, epipodophyllotoxins (e.g., Etoposide (VP-16), and Teniposide (VM-26), etc.), and agents that target topoisomerase I (e.g., Camptothecin and Isirinotecan (CPT-11), etc.); 2) covalent DNA-binding agents (alkylating agents), including, nitrogen mustards (e.g., Mechlorethamine, Chlorambucil, Cyclophosphamide, Ifosphamide, and Busulfan (Myleran), etc.), nitrosoureas (e.g., Carmustine, Lomustine, and Semustine, etc.), and other alkylating agents (e.g., Dacarbazine, Hydroxymethylmelamine, Thiotepa, and Mitocycin, etc.); 3) noncovalent DNA-binding agents (antitumor antibiotics), including, nucleic acid inhibitors (e.g., Dactinomycin (Actinomycin D), etc.), anthracyclines (e.g., Daunorubicin (Daunomycin, and Cerubidine), Doxorubicin (Adriamycin), and Idarubicin (Idamycin), etc.), anthracenediones (e.g., anthracycline analogues, such as, (Mitoxantrone), etc.), bleomycins (Blenoxane), etc., and plicamycin (Mithramycin), etc.; 4) antimetabolites, including, antifolates (e.g., Methotrexate, Folex, and Mexate, etc.), purine antimetabolites (e.g., 6-Mercaptopurine (6-MP, Purinethol), 6-Thioguanine (6-TG), Azathioprine, Acyclovir, Ganciclovir, Chlorodeoxyadenosine, 2-Chlorodeoxyadenosine (CdA), and 2'-Deoxycoformycin (Pentostatin), etc.), pyrimidine antagonists (e.g., fluoropyrimidines (e.g., 5-fluorouracil (Adrucil), 5-fluorodeoxyuridine (FdUrd) (Floxuridine)) etc.), and cytosine arabinosides (e.g., Cytosar (ara-C) and Fludarabine, etc.); 5) enzymes, including, L-asparaginase, and hydroxyurea, etc.; 6) hormones, including, glucocorticoids, such as, antiestrogens (e.g., Tamoxifen, etc.), nonsteroidal antiandrogens (e.g., Flutamide, etc.), and aromatase inhibitors (e.g., anastrozole (Arimidex), etc.); 7) platinum compounds (e.g., Cisplatin and Carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., Batimistat, etc.); and 17) other inhibitors of angiogenesis.

In preferred embodiments, the present invention provides administration of an effective amount of a water-soluble polymer-human ribonuclease conjugate and at least one conventional anticancer agent that kills cells (e.g., induces apoptosis) and/or prevents cancer cell proliferation to a subject. In some preferred embodiments, the subject has a disease characterized by metastasis. In yet other preferred embodiments, the present invention provides administration of an effective amount of a water-soluble polymer-human ribonuclease conjugate and a taxane (e.g., Docetaxel) to a subject having a disease characterized by the overexpression of Bcl-2 family protein(s) (e.g., Bcl-2 and/or Bcl-$X_L$).

The taxanes (e.g., Docetaxel) are an effective class of anticancer chemotherapeutic agents. (See, e.g., K. D. Miller and G. W. Sledge, Jr. Cancer Investigation, 17:121-136 (1999)). While the present invention is not intended to be limited to any particular mechanism, taxane-mediated cell death is thought to proceed through intercellular microtubule stabilization and subsequent induction of the apoptotic pathway. (See, e.g., S. Haldar et al., Cancer Research, 57:229-233 (1997)).

In some other embodiments, cisplatin and taxol are specifically contemplated for use with a water-soluble polymer-human ribonuclease conjugate composition of the present invention. Cisplatin and Taxol have a well-defined action of inducing apoptosis in tumor cells (See e.g., Lanni et al., Proc. Natl. Acad. Sci., 94:9679 (1997); Tortora et al., Cancer Research 57:5107 (1997); and Zaffaroni et al., Brit. J. Cancer 77:1378 (1998)). However, treatment with these and other chemotherapeutic agents is difficult to accomplish without incurring significant toxicity. The agents currently in use are generally poorly water soluble, quite toxic, and given at doses that affect normal cells as wells as diseased cells. For example, paclitaxel (Taxol), one of the most promising anticancer compounds discovered, is poorly soluble in water. Paclitaxel has shown excellent antitumor activity in a wide variety of tumor models such as the B16 melanoma, L1210 leukemias, MX-1 mammary tumors, and CS-1 colon tumor xenografts. However, the poor aqueous solubility of paclitaxel presents a problem for human administration. Accordingly, currently used paclitaxel formulations require a cremaphor to solubilize the drug. The human clinical dose range is 200-500 mg. This dose is dissolved in a 1:1 solution of ethanol:cremaphor and diluted to one liter of fluid given intravenously. The cremaphor currently used is polyethoxylated castor oil. It is given by infusion by dissolving in the cremaphor mixture and diluting with large volumes of an aqueous vehicle. Direct administration (e.g., subcutaneous) results in local toxicity and low levels of activity.

Any pharmaceutical that is routinely used in a cancer therapy context finds use in the present invention. Conventional anticancer agents that are suitable for administration with the disclosed water-soluble polymer-human ribonuclease conjugate compositions include, but are not limited to, adriamycin, 5-fluorouracil, etoposide, camptothecin, methotrexate, actinomycin-D, mitomycin C, or more preferably, cisplatin. These agent may be prepared and used as a combined therapeutic composition, or kit, by combining it with an immunotherapeutic agent, as described herein.

In some embodiments of the present invention, therapeutic treatments comprising a water-soluble polymer-human ribonuclease conjugate further comprise one or more agents that directly cross-link nucleic acids (e.g., DNA) to facilitate DNA damage (e.g., leading to a combination of agents that have synergistic or additive therapeutic properties). For example, agents such as cisplatin, and other DNA alkylating agents may be used. Cisplatin has been widely used to treat cancer, with efficacious doses used in clinical applications of 20 mg/$M^2$ for 5 days every three weeks for a total of three courses. The compositions of the present invention may be delivered via any suitable method, including, but not limited to, injection intravenously, subcutaneously, intratumorally, intraperitoneally, or topically (e.g., to mucosal surfaces).

Agents that damage DNA also include compounds that interfere with DNA replication, mitosis, and chromosomal segregation. Such chemotherapeutic compounds include, but are not limited to, adriamycin, also known as doxorubicin, etoposide, verapamil, podophyllotoxin, and the like. These compounds are widely used in clinical settings for the treatment of neoplasms, and are administered through bolus injections intravenously at doses ranging from 25-75 M/$^2$ at 21 day intervals for adriamycin, to 35-50 Mg/$M^2$ for etoposide intravenously or double the intravenous dose orally.

Agents that disrupt the synthesis and fidelity of nucleic acid precursors and subunits also lead to DNA damage and find use as chemotherapeutic agents in the present invention. A number of nucleic acid precursors have been developed. Particularly useful are agents that have undergone extensive testing and are readily available. As such, agents such as 5-fluorouracil (5-FU) are preferentially used by neoplastic tissue, making this agent particularly useful for targeting to neoplastic cells. The doses delivered may range from 3 to 15 mg/kg/day, although other doses may vary considerably according to various factors including stage of disease, amenability of the cells to the therapy, amount of resistance to the agents and the like.

In preferred embodiments, the anticancer agents (e.g., antiangiogenic factors discussed herein) used in the present invention are those that are amenable to co-administration with a water-soluble polymer-human ribonuclease conjugate such that they can be delivered into a subject, tissue, or cell without loss of fidelity of anticancer effect. For a more detailed description of cancer therapeutic agents such as a platinum complex, verapamil, podophyllotoxin, carboplatin, procarbazine, mechlorethamine, cyclophosphamide, camptothecin, ifosfamide, melphalan, chlorambucil, bisulfan, nitrosurea, adriamycin, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate and other similar anti-cancer agents, those of skill in the art are referred to any number of instructive manuals including, but not limited to, the Physician's Desk reference and to Goodman and Gilman's "Pharmaceutical Basis of Therapeutics" ninth edition, Eds. Hardman et al., 1996.

In some embodiments, the drugs are attached to a human ribonuclease with photocleavable linkers. For example, several heterobifunctional, photocleavable linkers that find use with the present invention are described (See, e.g., Ottl et al., Bioconjugate Chem., 9:143 (1998)). These linkers can be either water or organic soluble. They contain an activated ester that can react with amines or alcohols and an epoxide that can react with a thiol group. In between the two groups is a 3,4-dimethoxy6-nitrophenyl photoisomerization group, which, when exposed to near-ultraviolet light (365 nm), releases the amine or alcohol in intact form. Thus, the therapeutic agent, when linked to the compositions of the present invention using such linkers, may be released in biologically active or activatable form through exposure of the target area to near-ultraviolet light.

In an exemplary embodiment, an active group of a human ribonuclease is reacted with the activated ester of the organic-soluble linker. This product in turn is reacted with the partially-thiolated surface of appropriate dendrimers (the primary amines of the dendrimers can be partially converted to thiol-containing groups by reaction with a sub-stoichiometric amount of 2-iminothiolano). Thus conjugated, the drug is inactive and will not harm normal cells. When the conjugate is localized within tumor cells, it is exposed to laser light of the appropriate near-UV wavelength, causing the active drug to be released into the cell.

An alternative to photocleavable linkers are enzyme cleavable linkers. A number of enzyme cleavable linkers have been demonstrated as effective anti-tumor conjugates and can be prepared by attaching cancer therapeutics, such as doxorubicin, to water-soluble polymers with appropriate short peptide linkers (See e.g., Vasey et al., Clin. Cancer Res., 5:83 (1999)). The linkers are stable outside of the cell, but are cleaved by thiolproteases once within the cell. In a preferred embodiment, the conjugate PK1 is used. As an alternative to the photocleavable linker strategy, enzyme-degradable linkers, such as Gly-Phe-Leu-Gly may be used.

The present invention is not limited by the nature of the therapeutic technique. For example, other conjugates that find use with the present invention include, but are not limited to, using conjugated boron dusters for BNCT (See, e.g., Capala et al., Bioconjugate Chem., 7:7 (1996)), the use of radioisotopes, and conjugation of toxins such as ricin.

Antimicrobial therapeutic agents may also be used in combination with a water-soluble polymer-human ribonuclease conjugate as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins, antisense nucleic acids, membrane disruptive agents and the like, used alone or in combination. Indeed, any type of antibiotic may be used including, but not limited to, anti-bacterial agents, anti-viral agents, anti-fungal agents, and the like.

In still further embodiments, another component of the present invention is that a water-soluble polymer-human ribonuclease conjugate be associated with targeting agents that are able to specifically target a particular cell type (e.g., tumor cell). Generally, a targeting agent targets neoplastic cells through interaction of the targeting agent with a cell surface moiety and is taken into the cell through receptor mediated endocytosis.

Any moiety known to be located on the surface of target cells (e.g., tumor cells) finds use with the present invention. For example, an antibody directed against such a moiety targets the compositions of the present invention to cell surfaces containing the moiety. Alternatively, the targeting moiety may be a ligand directed to a receptor present on the cell surface or vice versa. Similarly, vitamins also may be used to target the therapeutics of the present invention to a particular cell.

In some embodiments of the present invention, the targeting moiety may also function as an agent to identify a particular tumor characterized by expressing a receptor that the targeting agent (ligand) binds with, for example, tumor specific antigens including, but not limited to, carcinoembryonic antigen, prostate specific antigen, tyrosinase, ras, a sialyly lewis antigen, erb, MAGE-1, MAGE-3, BAGE, MN, gp100, gp75, p97, proteinase 3, a mucin, CD81, CID9, CD63; CD53, CD38, CO-029, CA125, GD2, GM2 and O-acetyl GD3, M-TAA, M-fetal or M-urinary find use with the present invention. Alternatively the targeting moiety may be a tumor suppressor, a cytokine, a chemokine, a tumor specific receptor ligand, a receptor, an inducer of apoptosis, or a differentiating agent.

Tumor suppressor proteins contemplated for targeting include, but are not limited to, p16, p21, p27, p53, p73, Rb, Wilms tumor (WT-1), DCC, neurofibromatosis type 1 (NF-1), von Hippel-Lindau (VHL) disease tumor suppressor, Maspin, Brush-1, BRCA-1, BRCA-2, the multiple tumor suppressor (MTS), gp95/p97 antigen of human melanoma, renal cell carcinoma-associated G250 antigen, KS 1/4 pan-carcinoma antigen, ovarian carcinoma antigen (CA125), prostate specific antigen, melanoma antigen gp75, CD9, CD63, CD53, CD37, R2, CD81, C0029, TI-1, L6 and SAS. Of course these are merely exemplary tumor suppressors and it is envisioned that the present invention may be used in conjunction with any other agent that is or becomes known to those of skill in the art as a tumor suppressor.

In preferred embodiments of the present invention, targeting is directed to factors expressed by an oncogene (e.g., bcl-2 and/or bcl-$X_L$). These include, but are not limited to, tyrosine kinases, both membrane-associated and cytoplasmic forms, such as members of the Src family, serine/threonine kinases, such as Mos, growth factor and receptors, such as platelet derived growth factor (PDDG), SMALL GTPases (G proteins) including the ras family, cyclin-dependent protein kinases (cdk), members of the myc family members including c-myc, N-myc, and L-myc and bcl-2 and family members.

Receptors and their related ligands that find use in the context of the present invention include, but are not limited to, the folate receptor, adrenergic receptor, growth hormone receptor, luteinizing hormone receptor, estrogen receptor, epidermal growth factor receptor, fibroblast growth factor receptor, and the like.

Hormones and their receptors that find use in the targeting aspect of the present invention include, but are not limited to, growth hormone, prolactin, placental lactogen, luteinizing hormone, foilicle-stimulating hormone, chorionic gonadotropin, thyroid-stimulating hormone, leptin, adrenocorticotropin (ACTH), angiotensin I, angiotensin II, .alpha.-endorphin, .alpha. melanocyte stimulating hormone (α-MSH), cholecystokinin, endothelin I, galanin, gastric inhibitory peptide (GIP), glucagon, insulin, amylin, lipotropins, GLP-1 (7-37) neurophysins, and somatostatin.

In addition, the present invention contemplates that vitamins (both fat soluble and non-fat soluble vitamins) used as targeting agents may be used to target cells that have receptors for, or otherwise take up these vitamins. Particularly preferred for this aspect are the fat soluble vitamins, such as vitamin D and its analogues, vitamin E, Vitamin A, and the like or water soluble vitamins such as Vitamin C, and the like.

In some embodiments of the present invention, any number of cancer cell targeting groups are associated with a water-soluble polymer-human ribonuclease. Thus, a water-soluble polymer-human ribonuclease conjugate associated with targeting groups are specific for targeting cancer cells (i.e., much more likely to attach to cancer cells and not to healthy cells).

In preferred embodiments of the present invention, targeting groups are associated (e.g., covalently or noncovalently bound) to a water-soluble polymer-human ribonuclease with either short (e.g., direct coupling), medium (e.g., using small-molecule bifunctional linkers such as SPDP, sold by Pierce Chemical Company), or long (e.g., PEG bifunctional linkers, sold by Shearwater Polymers) linkages.

In preferred embodiments of the present invention, the targeting agent is an antibody or antigen binding fragment of an antibody (e.g., Fab units). For example, a well-studied antigen found on the surface of many cancers (including breast HER2 tumors) is glycoprotein p185, which is exclusively expressed in malignant cells (Press et al., Oncogene 5:953 (1990)). Recombinant humanized anti-HER2 monoclonal antibodies (rhuMabHER2) have even been shown to inhibit the growth of HER2 overexpressing breast cancer cells, and are being evaluated (in conjunction with conventional chemotherapeutics) in phase III clinical trials for the treatment of advanced breast cancer (Pegrarn et al., Proc. Am. Soc. Clin. Oncol., 14:106 (1995)). Park et al. have attached Fab fragments of rhuMabHER2 to small unilamellar liposomes, which then can be loaded with the chemotherapeutic doxorubicin (dox) and targeted to HER2 overexpressing tumor xenografts (Park et al., Cancer Lett., 118:153 (1997) and Kirpotin et al., Biochem., 36:66 (1997)). These dox-loaded "immunoliposomes" showed increased cytotoxicity against tumors compared to corresponding non-targeted dox-loaded liposomes or free dox, and decreased systemic toxicity compared to free dox.

In some embodiments, a targeting agent is an antibody-like moiety. Several antibody-like moieties are contemplated to useful in the present invention including, but not limited to, ankyrins, avimers, and lipocalins.

Antibodies can be generated to allow for the targeting of antigens or immunogens (e.g., tumor, tissue or pathogen specific antigens) on various biological targets (e.g., pathogens, tumor cells, normal tissue). Such antibodies include, but are not limited to polyclonal, monoclonal, chimeric, single chain, Fab fragments, and an Fab expression library.

In some preferred embodiments, the antibodies recognize tumor specific epitopes (e.g., TAG-72 (Kjeldsen et al., Cancer Res. 48:2214-2220 (1988); U.S. Pat. Nos. 5,892,020; 5,892,019; and 5,512,443); human carcinoma antigen (U.S. Pat. Nos. 5,693,763; 5,545,530; and 5,808,005); TP1 and TP3 antigens from osteocarcinoma cells (U.S. Pat. No. 5,855,866); Thomsen-Friedenreich (TF) antigen from adenocarcinoma cells (U.S. Pat. No. 5,110,911); "KC-4 antigen" from human prostrate adenocarcinoma (U.S. Pat. Nos. 4,708,930 and 4,743,543); a human colorectal cancer antigen (U.S. Pat. No. 4,921,789); CA125 antigen from cystadenocarcinoma (U.S. Pat. No. 4,921,790); DF3 antigen from human breast carcinoma (U.S. Pat. Nos. 4,963,484 and 5,053,489); a human breast tumor antigen (U.S. Pat. No. 4,939,240); p97 antigen of human melanoma (U.S. Pat. No. 4,918,164); carcinoma or orosomucoid-related antigen (CORA) (U.S. Pat. No. 4,914,021); a human pulmonary carcinoma antigen that reacts with human squamous cell lung carcinoma but not with human small cell lung carcinoma (U.S. Pat. No. 4,892,935); T and Tn haptens in glycoproteins of human breast carcinoma (Springer et al., Carbohydr. Res. 178:271-292 (1988)), MSA breast carcinoma glycoprotein termed (Tjandra et al., Br. J. Surg. 75:811-817 (1988)); MFGM breast carcinoma antigen (Ishida et al., Tumor Biol. 10:12-22 (1989)); DU-PAN-2 pancreatic carcinoma antigen (Lan et al., Cancer Res. 45:305-310 (1985)); CA125 ovarian carcinoma antigen (Hanisch et al., Carbohydr. Res. 178:29-47 (1988)); YH206 lung carcinoma antigen (Hinoda et al., Cancer J., 42:653-658 (1988)). Each of the foregoing references are specifically incorporated herein by reference.

For breast cancer, the cell surface may be targeted with folic acid, EGF, FGF, and antibodies (or antibody fragments) to the tumor-associated antigens MUC1, cMet receptor and CD56 (NCAM).

In some embodiments of the present invention, the targeting agents are preferably nucleic acids (e.g., RNA or DNA). In some embodiments, the nucleic acid targeting agents are designed to hybridize by base pairing to a particular nucleic acid (e.g., chromosomal DNA, mRNA, or ribosomal RNA). In other embodiments, the nucleic acids bind a ligand or biological target. Nucleic acids that bind the following proteins have been identified: reverse transcriptase, Rev and Tat proteins of HIV (Tuerk et al., Gene, 137(1):33-9 (1993)); human nerve growth factor (Binkley et al., Nuc. Acids Res., 23(16):3198-205 (1995)); and vascular endothelial growth factor (Jellinek et al., Biochem., 83(34):10450-6 (1994)). Nucleic acids that bind ligands are preferably identified by the SELEX procedure (See e.g., U.S. Pat. Nos. 5,475,096; 5,270,163; and 5,475,096; and in PCT publications WO 97/38134, WO 98/33941, and WO 99/07724, all of which are herein incorporated by reference), although many methods are known in the art.

EXPERIMENTAL

The following examples are provided in order to demonstrate and further illustrate certain preferred embodiments and aspects of the present invention and are not to be construed as limiting the scope thereof.

Example 1

Pegylation of Bovine RNase A with N-hydroxy succinimide (NHS) Linear 20 k mPEG

NHS mPEG was added as a dry powder to RNase A (50 mM HEPES, 5 mM $CaCl_2$, 5 mM $MgCl_2$, pH 7.5) in three different ratios: 1:1, 1:3, and 1:10 of RNase:PEG. The reaction mixtures were incubated for one hour at room temperature with occasional vortexing and then overnight at 4° C. without vortexing.

When analyzed by SDS PAGE, the 1:1 RNase:PEG reaction had predominantly unreacted RNase and a 1:1 RNase:PEG conjugate (See FIG. 2). RNase:PEG conjugates of 1:1, 1:2, and 1:3 RNase PEG are the predominant products for the 1:3 and 1:10 RNase:PEG reactions.

Example 2

Pegylation of RNase with an aldehyde Linear 30 k mPEG

Figure 3:
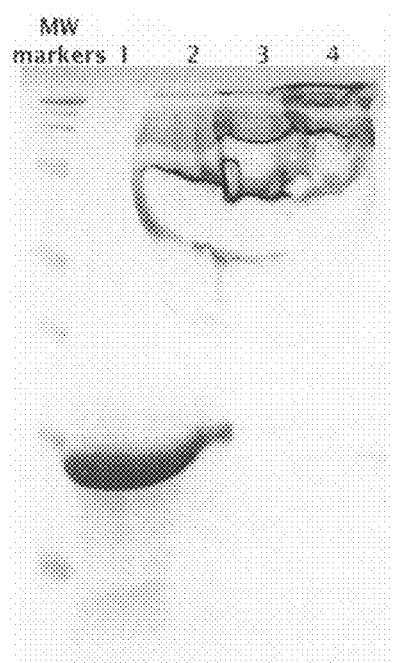
FIG. 3 shows an SDS-PAGE run on four samples of RNase conjugated with an aldehyde linear 30 kD mPEG: (1) wild type RNase A; (2) RNase:PEG (1:2) reaction; (3) RNase:PEG (1:4) reaction; and (4) RNase:PEG (1:8) reaction. A molecular weight ladder is provided for comparison (MW markers).

Aldehyde mPEG was added to RNase A (50 mM HEPES, pH 5.0, 20 mM $NaCNBH_3$) in three different ratios: 1:2, 1:4, and 1:8 RNase:PEG. The reaction mixtures were incubated at 4° C. overnight with slow stirring. When analyzed by SDS-PAGE, conjugates of 1:1, 1:2, and 1:3 RNase:PEG were present to varying extents in each of the conjugation reactions (See FIG. 3). The 1:1 and 1:2 RNase:PEG conjugates are present in roughly equal amounts in the reaction mixture of 1:4 RNase:PEG.

Figure 4:
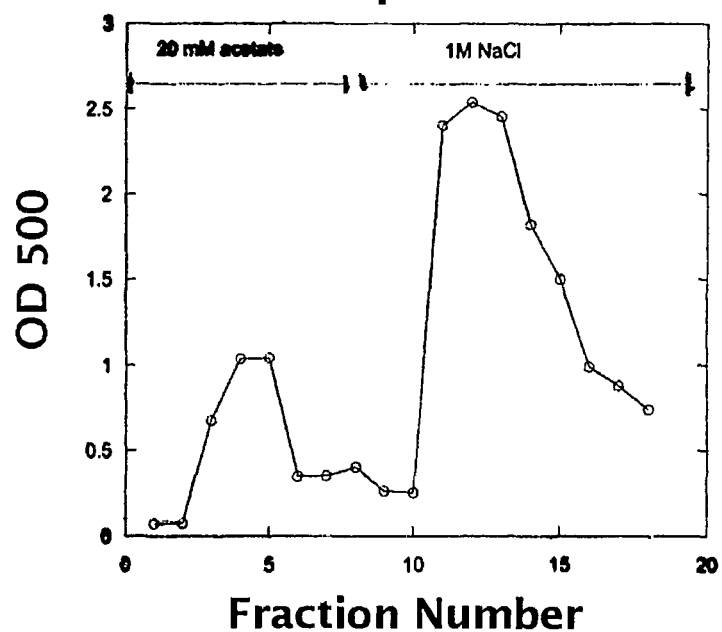
FIG. 4 shows fractions from a cation exchange column tested for the presence of PEG.
Figure 5:
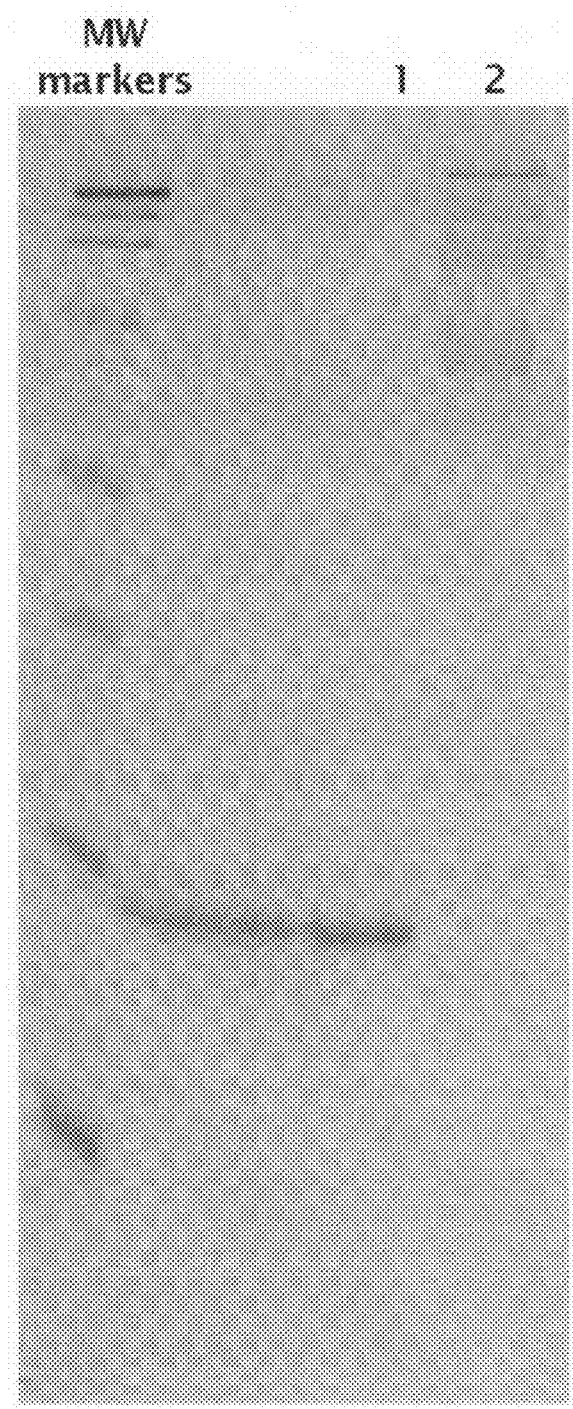
FIG. 5 shows an SDS-PAGE run on two samples: (1) wild type RNase A and (2) Partially purified RNase:PEG (1:4). A molecular weight ladder is provided for comparison (MW markers).

The 1:4 RNase:PEG reaction mixture product was dialyzed overnight (20 mM Na acetate, pH 5.0) and run over a cation exchange column (SP-Sepharose fast flow; Pharmacia; eluted with 20 mM sodium acetate, 1 M NaCl, pH 5.0). Fractions were collected and tested for the presence of PEG (1 g NaI+0.5 g $I_2$ in 50 mL $H_2O$). Two sets of PEG-containing species were separated on the column, shown as two separate peaks on the column (See FIG. 4). Four fractions from the second peak were combined and SDS-PAGE performed along with a sample of RNase A for comparison. The semi-purified sample contains multiple conjugates with varying numbers of PEG to RNase (See FIG. 5). Thus, in some embodiments, the present invention provides a composition comprising RNase:PEG conjugates wherein the population of conjugates have a mixed degree of conjugation (e.g., present in the population of conjugates are conjugates that have ratios of RNase:PEG of 1:1, 1:2, 1:3 and/or more than three PEG molecules per molecule of RNase. In some embodiments, the population of conjugates can be purified (e.g., using the methods described herein) in order to generate a population predominantly comprises RNase molecules conjugated to the same number of PEG molecules (e.g., wherein greater than 50%, greater than 60%, greater than 70%, greater than 80%, greater than 90%, greater than 95%, greater than 97%, greater than 98%, or more of the RNase molecules in the population are conjugated to the same number of PEG molecules (e.g., 1, 2 , 3, 4, 5, or more PEG molecules).

Example 3

Pegylation of Human RNase 1 with butyl aldehyde mPEGs

Pegylation of wild type pancreatic ribonuclease 1 was performed with butyl aldehyde mPEGs (e.g., linear 30 kDa, branched 40 kDa, or branched 60 kDa). A 1:3 ratio of PEG:RNase was used, and the reaction performed at three different pH conditions. The buffers used were citric acid (0.1M citric acid, 0.15M NaCl at pH 5 or pH 6) and sodium phosphate (0.1M NaH$_2$PO$_4$, 0.15M NaCl at pH 7).

Twelve milligrams of the butyl aldehyde linear 30 kDa mPEG was added to RNase 1 in citric acid at pH 5.0 (203 μl of a 9.86 mg/mL solution). The reaction was incubated overnight. Sodium cyanoborohydride (2 μl of a 5M solution in 1 M NaOH; Aldrich) was added, and the reaction incubated for thirty minutes. Tris-HCl (10 μl of a 1M solution) was added to the reaction, and the reactions incubated for an additional 30 minutes at room temperature. The other reactions were run under the same conditions with different pH (controlled by the choice of buffer) and different mPEGs.

An SDS-PAGE was run that included each reaction mixture as well as the controls of wild type RNase 1 and a molecular weight ladder. The samples were all heated (except the molecular weight ladder) at 90° C. for five minutes and loaded onto a 12% BisTris CRITERION XT gel (BioRad). The gel was run at 200V for 50 minutes using XTMES buffer (BioRad). The dilution buffer was PBS, pH 7.44, and the loading buffer was 50% sample buffer, 40% deionized water, and 10% reducing agent.

Figure 6:
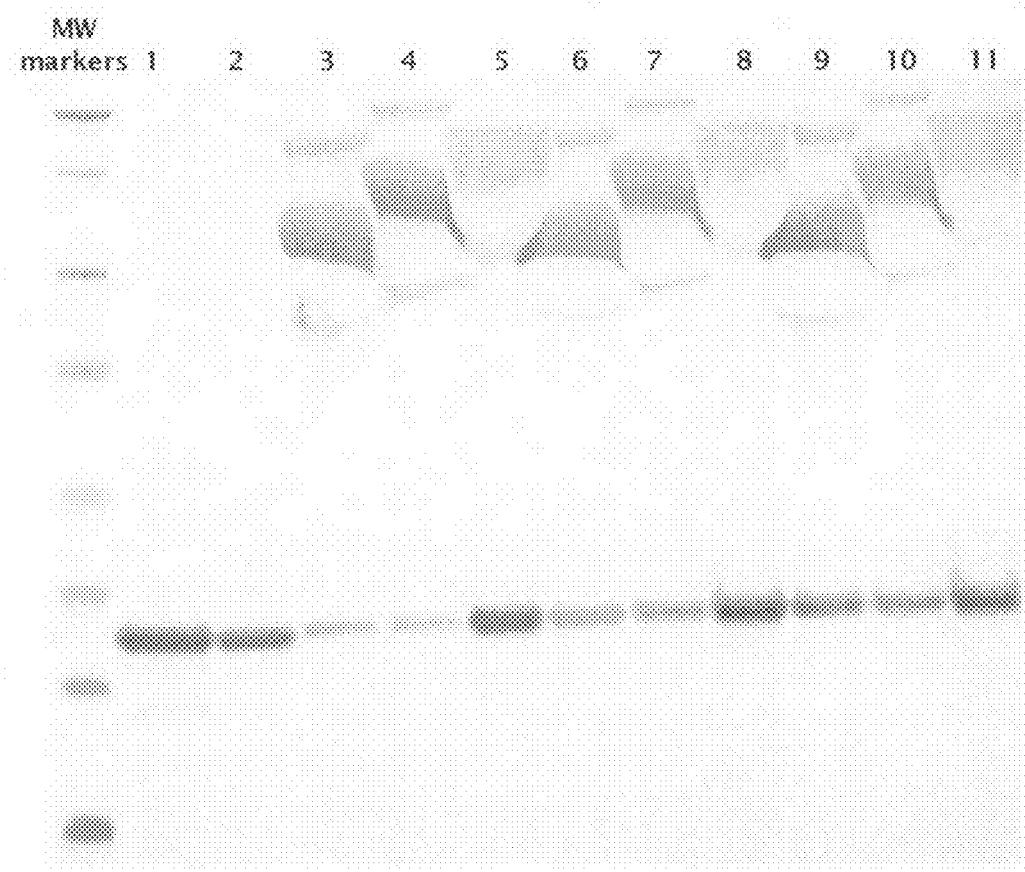
FIG. 6 shows an SDS page of the following RNase 1 conjugates: (1) wild type RNase 1; (2) wild type RNase 1; (3) RNase 1+30 kDa PEG, pH 5; (4) RNase 1+40 kDa PEG, pH 5; (5) RNase 1+60 kDa PEG, pH 5; (6) RNase 1+30 kDa PEG, pH 6; (7) RNase 1+40 kDa PEG, pH 6; (8) RNase 1+60 kDa PEG, pH 6; (9) RNase 1+30 kDa PEG, pH 7; (10) RNase 1+40 kDa PEG, pH 7; (11) RNase 1+60 kDa PEG, pH 7. A molecular weight ladder is provided for comparison (MW markers).
Figure 7:
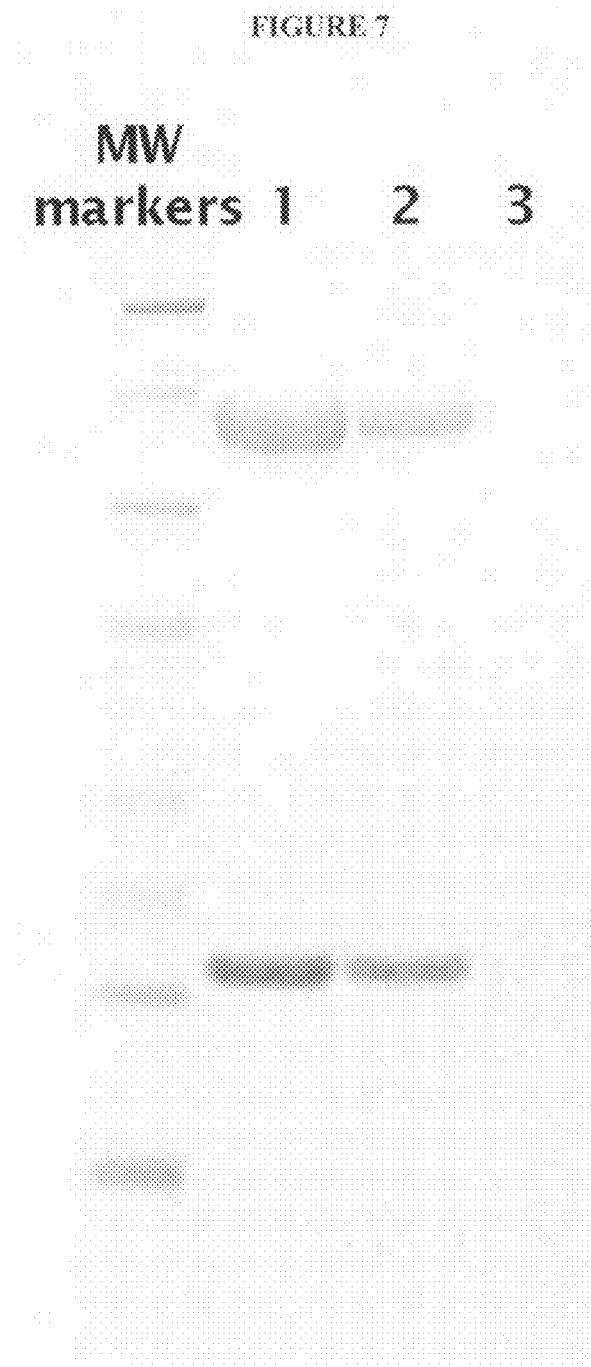
FIG. 7 shows SDS-PAGE of samples of the first step (anion exchange) of the purification procedure for the linear 30 kDa mPEG-RNase 1 of Example 4: (1) Sample loaded onto anion exchange column; (2) Flow through from the anion exchange column; (3) Material eluted from anion exchange column. A molecular weight ladder is provided for comparison (MW markers).

Under the reaction conditions described, the completeness (e.g., the percentage of RNase 1 protein conjugated to polymer at the completion of the reaction) of the reactions follows the order of pH 5>pH 6>pH 7 (See FIG. 6). The reactions utilizing the 30 kDa and 40 kDa mPEGs were further complete (e.g., comprised more RNase:PEG conjugates) than the reactions using 60 kDa mPEG. The reactions each contained a majority population of conjugates of a single PEG to a single RNase (See FIG. 6).

In some embodiments, the present invention provides a composition comprising human RNase:PEG conjugates wherein the population of conjugates have a mixed degree of conjugation (e.g., present in the population of conjugates are conjugates that have ratios of RNase:PEG of 1:1, 1:2, 1:3 and/or more than three PEG molecules per molecule of RNase. In some embodiments, the present invention provides a composition comprising human RNase:PEG-conjugates wherein the population of conjugates comprises RNase molecules conjugated to the same number of PEG molecules. In some embodiments, the population of conjugates can be purified (e.g., using the methods described herein) in order to further purify the conjugate population (e.g., to generate a population predominantly comprising RNase molecules conjugated to the same number of PEG molecules (e.g., wherein greater than 50%, greater than 60%, greater than 70%, greater than 80%, greater than 90%, greater than 95%, greater than 97%, greater than 98%, or more of the RNase molecules in the population are conjugated to the same number of PEG molecules (e.g., 1, 2, 3, 4, 5, or more PEG molecules).

Example 4

Scale Up Production and Purification of Conjugates of RNase 1 and the butyl aldehyde Linear 30 k and Branched 40 k mPEG A 1:1 ratio of PEG to RNase 1 was used in the following reactions. Eight milliliters of a solution containing 10.28 mg/mL of RNase 1 in 0.1M citric acid, 0.15M NaCl at pH 5 was added to either 30 kDa mPEG (164.5 mg) or 40 kDa mPEG (219.4 mg) and was incubated at 4° C. overnight.

Sodium cyanoborohydride (80 μl of 5M in 1M NaOH) was added, and the mixture incubated for 30 minutes at room temperature. Tris (400 μl of 1M, pH 7) was added, and the solution incubated for 30 minutes at room temperature.

Each reaction was diluted with 40 mL of 5% 20 mM Tris acetate, 2.0 M NaCl, pH 8.0 and the pH adjusted to ~8 by dropwise addition of ~600 μl of 1M NaOH. The reaction was run over an anion exchange column and the flow through collected.

SDS PAGE (BioRad XT Gel) was used to characterize the starting material as well as the purified product. The running buffer was XTMES, the dilution buffer was PBS, and the loading buffer was XT. All samples except the molecular weight markers were heated at 90° C. for 5 minutes. The gel was run at 125V for 1.5 hr.

At 9.2° C., the pH of the solution was 8.45, and the pH was adjusted to 5.01 at 10.1° C. with approximately 300 μl of acetic acid. The solution was loaded onto a cation exchange column equilibrated in 20 mM Tris acetate, pH 5.0 and baseline separation of conjugate and wild type RNase 1 was achieved eluting with a sodium chloride gradient in the tris acetate buffer.

Figure 8:
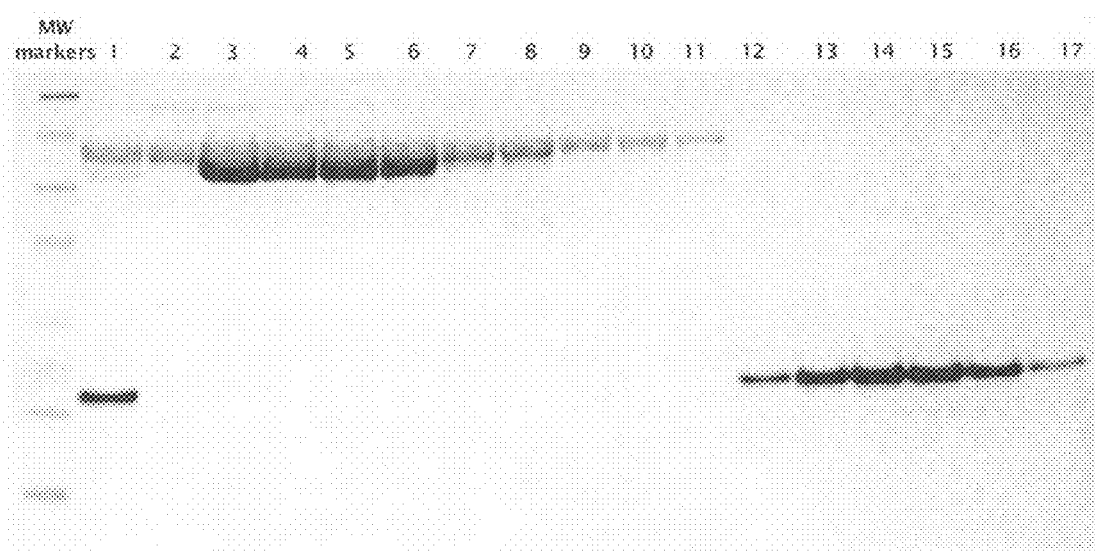
FIG. 8 shows SDS-PAGE of samples from the second step (cation exchange chromatography) of the purification procedure for the linear 30 kDa mPEG-RNase conjugate of Example 4: (1) Sample loaded onto the cation exchange column; (2-17) Fractions from cation exchange column. A molecular weight ladder is provided for comparison (MW markers).

SDS PAGE (BioRad XT Gel) was used to characterize the starting material as well as the purified product (See FIG. 8). The running buffer was XTMES, the dilution buffer was PBS, and the loading buffer was XT. All samples except the molecular weight markers were heated at 90° C. for 5 minutes. The gel was run at 125V for 1.5 hr.

Figure 9:
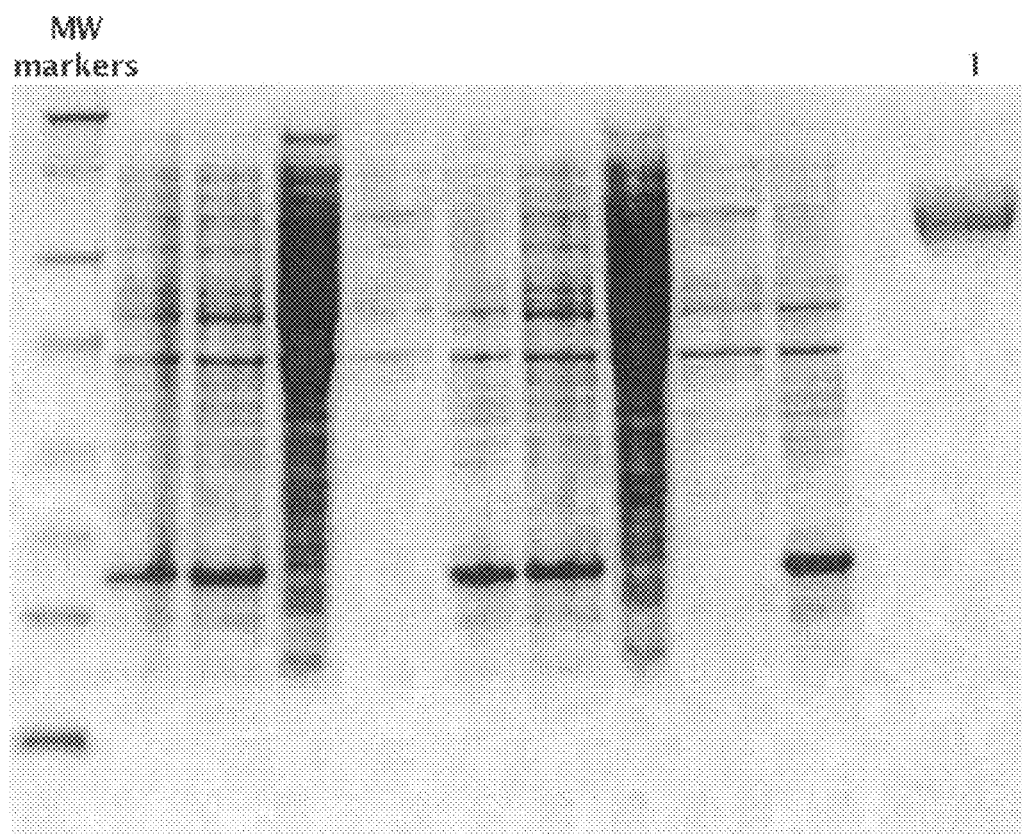
FIG. 9 shows SDS-PAGE after the purification of the conjugate was completed: (1) Final purified product (butyl aldehyde linear 30 kDa mPEG-RNase conjugate). A molecular weight ladder is provided for comparison (MW markers).

The purity of the column fractions was analyzed by SDS-PAGE in order to pool fractions for at least 95% purity (See FIG. 9). The concentration of protein in each sample was determined using an absorbance extinction coefficient of $\epsilon_{1\ cm}^{0.1\%}=0.174$ at 280 nm. The concentration was 2.06 mg/mL. The final volume was 62 mL, indicating a yield of 127 mg.

Example 5

Determination of Enzymatic Activity

The enzymatic activity of the PEG-RNase conjugate was determined using a fluorescent assay based on fluorescence resonance energy transfer (FRET). The substrate for the assay, 5'FAM-ArUAA-3'TAMRA (IDT), is not fluorescent until cleaved.

The buffer (160 microliters of 100 mM NaCl, 100 mM Tris, pH 7.0, 100 microgram/mL BSA) was added to the wells of a 96-well non-binding surface, black, polystyrene plate. The RNase whose activity is to be determined is added (typically 10 μl of an approximately $2 \times 10^{-10}$ M solution). Substrate (30 μl of a 1.33 μM solution of 5'FAM-ArUAA-3'TAMRA) is then added to each well, and the samples mixed. The plate is read on a fluorescent plate reader immediately.

Control wells were included for F0 (no enzyme) and Fmax determinations (typically 10 μl of a 0.1 mg/mL solution of RNase A per 200 μl assay). The $k_{cat}/K_M$ for the linear 30 kDa PEG:RNase conjugate was $2.7 \times 10^7$ $M^{-1} sec^{-1}$, as compared to the wild type human RNase 1 which had a $k_{cat}/K_M = 1.7 \times 10^7$ $M^{-1} sec^{-1}$. The $k_{cat}/K_M$ for the branched 40 kDa PEG:RNase conjugate was $2.62 \times 10^7$ $M^{-1} sec^{-1}$ (See FIG. 10). Thus, the present invention provides that, in some embodiments, conjugation of PEG molecules to human RNase provides human RNase molecules that retain enzymatic activity.

Example 6

Characterization of the PEG:RNase 1 Conjugates in a Xenograft Model of Non-Small Cell Lung Cancer Cells from a non-small cell lung cancer cell line (A549) were grown in nine T175 flasks in F12K media and 10% fetal calf serum until the cells were confluent. $4.5 \times 10^6$ cells (in 100 μl) were injected into the right rear flank of 4-5 week old male homozygous (nu/nu) nude mice (Harlan, Madison Wis.). Tumors were allowed to grow to an average size of ≥75 mm³ before treatments were initiated. Animals of each tumor type, with the properly sized tumors, were divided into treatment groups, including one set of animals treated weekly with vehicle (phosphate buffered saline, PBS). The vehicle and the test agents were all administered by intraperitoneal injection. Each animal was weighed twice a week during treatment. The tumors were measured twice weekly using calipers. Tumor volume (mm³) was determined by using the formula for an ellipsoid sphere:

$$volume = \frac{l \times w^2}{2}$$

The percent tumor growth inhibition was calculated using the formula:

$$\%TGI = 1 - \frac{(final\ size - starting\ size)_{treated}}{(final\ size - starting\ size)_{control}} \times 100$$

The efficacy of the linear 30 kDa PEG:RNase conjugate is shown relative to cisplatin (See FIG. 11). The conjugate was administered at 75 mg of total conjugate per kg of body weight of the animal (75 mg/kg 1×wk), while the cisplatin was used at 6 mg/kg once a week. The value of n represents the number of animals in the specific treatment arm of the experiment.

The efficacy of the branched 40 kDa PEG:RNase conjugate is also shown relative to cisplatin (See FIG. 12). The conjugate was administered at 75 mg of total conjugate per kg of body weight of the animal (75 mg/kg 1×wk), while the cisplatin was used at 6 mg/kg once a week. The value of n represents the number of animals in the specific treatment arm of the experiment.

Thus, the present invention provides a composition comprising human RNase-PEG conjugates, wherein the conjugates possess tumor growth inhibition properties. In some embodiments, a conjugate of the present invention display less tumor growth inhibition than cisplatin (e.g., linear 30 kDa PEG:RNase conjugate). In some embodiments, a conjugate of the present invention displays more tumor growth inhibition than cisplatin (e.g., branched 40 kDa PEG:RNase conjugate). In some embodiments, a conjugate of the present invention displays less toxicity to a host subject than cisplatin (e.g., linear 30 kDa PEG:RNase conjugate or branched 40 kDa PEG:RNase conjugate). In some embodiments, the present invention provides a conjugate that displays superior tumor growth inhibition (e.g., of non-small cell lung tumors) compared to cisplatin while concurrently being less toxic to a host than cisplatin (e.g., branched 40 kDa PEG:RNase conjugate).

Example 7

Characterization of the PEG:RNase 1 Conjugates in a Xenograft Model of Breast Cancer Cells from a breast cancer cell line (MDA-MB-231) were grown in seven T175 flasks in RPMI-1640 media and 10% fetal calf serum until the cells were confluent. $5.6 \times 10^6$ cells (in 100 μl) were injected into the right rear flank of 4-5 week old female homozygous (nu/nu) nude mice (Harlan, Madison Wis.). Tumors were allowed to grow to an average size of ≥75 mm³ before treatments were initiated. Animals of each tumor type, with the properly sized tumors, were divided into treatment groups, including one set of animals treated weekly with vehicle (phosphate buffered saline, PBS). The vehicle and the test agents were all administered by intraperitoneal injection. Each animal was weighed twice a week during treatment. The tumors were measured twice weekly using calipers. Tumor volume (mm³) and percent tumor growth inhibition were determined using the formulas described above.

The efficacy of the branched 40 kDa PEG:RNase conjugate is shown relative to doxorubicin (See FIG. 13). The conjugate was administered at 75 mg of total conjugate per kg of body weight of the animal (75 mg/kg 1×wk), while the doxorubicin was used at 3 mg/kg once a week. The value of n represents the number of animals in the specific treatment arm of the experiment.

Thus, the present invention provides a composition comprising human RNase-PEG conjugates, wherein the conjugates possess tumor growth inhibition properties. In some embodiments, a conjugate of the present invention displays more tumor growth inhibition than doxorubicin (e.g., branched 40 kDa PEG:RNase conjugate). In some embodiments, a conjugate of the present invention displays less toxicity to a host subject than doxorubicin (e.g., branched 40 kDa PEG:RNase conjugate). In some embodiments, the present invention provides a conjugate that displays superior tumor growth inhibition (e.g., of breast cancer tumors) compared to doxorubicin while concurrently being less toxic to a host than doxorubicin (e.g., branched 40 kDa PEG:RNase conjugate). Thus, the present invention provides a method of inhibiting tumor growth in a subject. The present invention is not limited by the type of tumor whose growth is inhibited by compositions of the present invention. Indeed, a variety of tumors can be treated using the compositions and methods of the present invention including, but not limited to, lung cancer, breast cancer, epithelial cancer, prostate cancer, and other cancers known to be treatable (e.g., whose growth is inhibited) with cisplatin and doxorubicin.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of treating cancer in a subject comprising administering to said subject a composition comprising human ribonuclease 1 conjugated to polyethylene glycol at amino acid residues 1, 49, 75, or 113, and wherein said human ribonuclease 1 retains a biologic activity, and wherein said treatment results in reduction in at least one tumor in said subject.

2. A method of treating a subject with cancer comprising administering to said subject a composition comprising human ribonuclease 1 conjugated to polyethylene glycol at amino acid residues 1, 49, 75, or 113, and wherein said composition is administered to said subject under conditions such that tumor growth associated with said cancer is inhibited.

3. The method of Claim 2, wherein said polyethylene glycol is between 20 and 100 kDa.

4. The method of Claim 2, wherein said polyethylene glycol is selected from the group consisting of linear polyethylene glycol and branched polyethylene glycol.

5. The method of Claim 2, wherein said polyethylene glycol is branched 40 kDa polyethylene glycol.

* * * * *